United States Patent
Summar et al.

(10) Patent No.: US 10,265,286 B2
(45) Date of Patent: *Apr. 23, 2019

(54) SEQUELAE OF CARDIOPULMONARY BYPASS-INDUCED PULMONARY INJURY

(71) Applicant: Vanderbilt University, Nashville, TN (US)

(72) Inventors: Marshall L. Summar, Washington, DC (US); Frederick W. Barr, Little Rock, AR (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,248

(22) Filed: Dec. 22, 2017

(65) Prior Publication Data

US 2018/0214403 A1    Aug. 2, 2018

Related U.S. Application Data

(60) Provisional application No. 62/439,772, filed on Dec. 28, 2016.

(51) Int. Cl.
 *A61K 31/198* (2006.01)

(52) U.S. Cl.
 CPC .................. *A61K 31/198* (2013.01)

(58) Field of Classification Search
 CPC ................................ A61K 31/198
 See application file for complete search history.

(56) References Cited

U.S. PATENT DOCUMENTS

| | | |
|---|---|---|
| 6,346,382 B1 | 2/2002 | Summar |
| 6,743,823 B1 | 6/2004 | Summar |
| 8,188,147 B2 | 5/2012 | Summar et al. |
| 8,536,225 B2 | 9/2013 | Summar et al. |
| 9,486,429 B2 | 11/2016 | Summar et al. |
| 2008/0234379 A1 | 9/2008 | Summar et al. |
| 2012/0252895 A1* | 10/2012 | Summar ............... A61K 31/19 |
| | | 514/564 |

FOREIGN PATENT DOCUMENTS

| | | |
|---|---|---|
| EP | 1690535 | 4/2015 |
| EP | 2361621 | 8/2017 |
| WO | 200909999 | 8/2009 |
| WO | 2009099998 | 8/2009 |
| WO | 2017004233 | 5/2017 |

OTHER PUBLICATIONS

Barr et al. (The J of Thoracic and Cardiovascular Surgery, 134, 2, p. 319-326, 2007.*
Vadivel et al. Pediatric Research (2010) 68(6): 519-525.
Pearson et al. The New England Journal of Medicine (2001) 344(24): 1832-1838.
International Search Report dated Feb. 22, 2018 from International Patent Application No. PCT/US2017/068698.
Written Opinion dated Feb. 22, 2018 from International Patent Application No. PCT/US2017/68698.

* cited by examiner

*Primary Examiner* — Savitha M Rao
(74) *Attorney, Agent, or Firm* — Hunton Andrews Kurth LLP

(57) ABSTRACT

A method for administering citrulline to a patient during surgery without filtration of the hemolysis to reduce the uncoupling of eNOS enzyme dimer that leads to cardiopulmonary bypass-induced pulmonary injury.

14 Claims, 26 Drawing Sheets

PK Parameters

| Dose (mg/kg) | $R_{app}$ (μmol/hr/kg) | $K_{rem}$ (hr$^{-1}$) | $V_d$ (L/kg) |
|---|---|---|---|
| 50 | 21.3 | 0.69 | 1.36 |
| 100 | 22.3 | 0.69 | 1.44 |
| 150 | 20.1 | 0.72 | 1.17 |

Note: Time on inotropes is censored at 48 hours if patient was still receiving inotropes at hour 48.

Note: Time on inotropes is censored at 48 hours if patient was still receiving inotropes at hour 48.

Note: Time on vasoactive medications is censored at 48 hours if patient was still receiving vasoactive medications at hour 48.

Note: Time on vasoactive medications was censored at 48 hours if a patient was still receiving vasoactive medications at this time point.

Note: Longest duration was censored if the duration of inotrope or vasodilator use was 48 hours.

SEQUELAE OF CARDIOPULMONARY BYPASS-INDUCED PULMONARY INJURY

CROSS-REFERENCE TO RELATED APPLICATIONS

This patent application claims priority to U.S. Provisional Patent Application No. 62/440,219, filed Dec. 29, 2016, the contents of which is incorporated herein by reference in its entirety.

FIELD OF THE INVENTION

The present invention relates generally to the field of the maintaining the coupling of endothelial nitric oxide synthase (eNOS) to reduce the incidence or severity of cardiopulmonary bypass-induced pulmonary injury due to free radical formation in a patient during cardiopulmonary bypass comprising administering an effective amount of citrulline to the patient.

BACKGROUND OF THE INVENTION

Sequelae of Cardiopulmonary Bypass-Induced Pulmonary Injury

In the immediate post-operative period, children who have undergone surgery to repair a congenital heart lesion are highly vulnerable to a sudden or sustained increase in pulmonary vascular resistance. Following surgery, the reactivity of the pulmonary vasculature is increased such that vasospastic stimuli may cause sudden increases in pulmonary arterial pressure and resistance. These in turn may lead to acute right-sided heart failure, tricuspid regurgitation, systemic hypotension, myocardial ischemia, and increased airway resistance. In their full-blown form, such pulmonary hypertensive crises may be lethal. Milder stimulating events can precipitate milder crises that last longer and cluster, leading to prolonged stays in the Intensive Care Unit (ICU). Adatia & Beghetti (2009) *Cardiol Young* 19(4): 315-319.

Cardiopulmonary bypass (CPB) induced injury results from a principally humoral systemic inflammatory response induced by the bypass process. Seghaye (2003) *Cardiol Young* 13(3): 228-239; Day & Taylor (2005) *Int J Surg* 3(2): 129-140; Jaggers & Lawson (2006) *Ann Thorac Surg* 81(6): S2360-2366; Kozik & Tweddell (2006) *Ann Thorac Surg* 81(6): S2347-2354; Warren et al. (2009) *J Cardiothorac Vasc Anesth* 23(2): 223-231; Warren et al. (2009) *J Cardiothorac Vasc Anesth* 23(3): 384-393. The damage sustained by the lung and other tissues results in the serious clinical condition described herein.

Proportion of Children Undergoing CPB Who Develop Pulmonary Injury Sequelae to CPB About one fifth to one third of juvenile patients undergoing cardiopulmonary bypass suffer from sequelae of cardiopulmonary bypass-induced pulmonary injury. Acute postoperative pulmonary hypertension is considered a key feature indicative of sequelae of cardiopulmonary bypass-induced pulmonary injury. Russell provides criteria to clinically significant pulmonary hypertension as either: (A) where the mean pulmonary arterial pressure was ≥50% of the mean systemic arterial pressure; or (B) where echocardiographic data indicated a similar degree of pulmonary hypertension. Russell et al. (1998) *Anesth Analg* 87(1): 46-51. This resulted in a figure of 13 of 36, or 36% of patients undergoing congenital heart repair surgery suffering from sequelae of cardiopulmonary bypass-induced pulmonary injury.

In another approach, Lindberg focused upon severe pulmonary hypertension by defining severe postoperative pulmonary hypertension as a mean pulmonary arterial pressure equal to or exceeding the level of mean systemic arterial pressure. Lindberg et al. (2002) *J Thorac Cardiovasc Surg* 123(6): 1155-1163. Overall, 2% of 1349 patients in their population met this stringent criteria. Lindberg discusses the presence of moderate cases of pulmonary hypertension, but did not specifically quantitate them. However, patients who qualified for full chart review either had a pulmonary arterial catheter in the ICU, spent more than four days on mechanical ventilation, or died. These patients, who likely had clinically significant pulmonary hypertension, totaled 224 in number, representing 17% of the population. Id.

A number of studies cite similar figures. Bando mentions about 30% percent of patients historically developed pulmonary hypertension while noting a more recent decrease, however the data in the paper suggest an about 17% rate. Bando et al. (1996) *J Thorac Cardiovasc Surg* 112(6): 1600-1607. Checchia stated that the exact incidence of pulmonary hypertension in children undergoing cardiac surgery remains unclear. Checchia et al. (2012) *Pediatr Cardiol* 33(4): 493-505. Checchia noted only one study where 11 of 20 infants developed postoperative pulmonary hypertension; when episodic pulmonary hypertension cases were also included, the proportion rose to 75%. Id.

Fate of Children Who Develop Post-Operative Pulmonary Hypertension

A study by Brown examined the fate of children who develop postoperative pulmonary hypertension and framed it in clinically and economically important terms. All possible risk factors for length of stay were examined in several multivariate models. The strongest factors, including pulmonary hypertension, were combined into a complications score. Both in the postoperative model and in the final model as part of the complications score, pulmonary hypertension was a strong predictor of prolonged length of stay. Prolonged length of stay has major economic consequences. Children who fell above the 95$^{th}$ percentile for length of stay accounted for 30% of bed days with three-times the mortality of children under the 95$^{th}$ percentile. In one center, 7.1% of patients used 50.1% of the total intensive care days and 47.7% of the total technology resources. Notably, 12% of patients required ICU stays of 14 days or longer. For all patients, the median stay was 3 days. In contrast, the median ICU stay of patients at or above the 95$^{th}$ percentile was 27 days. Consistent with this, the median duration of mechanical ventilation for patients at or above the 95$^{th}$ percentile was 23 days. Brown et al. (2003) *Crit Care Med* 31(1): 28-33.

Current Therapies for Sequelae of CPB-Induced Pulmonary Injury

Landis provided an evidence-based review of the various strategies in use to treat postoperative pulmonary hypertension in adult pulmonary bypass, concluding that only inhaled nitric oxide and possibly complement inhibitors provide any real value. Landis et al. (2014) *J Extra Corpor Technol* 46(3): 197-211. Other studies have focused upon pediatric cardiac surgery. Apostolakis et al. (2010) *J Cardiothorac Surg* 5: 1; Barst et al. (2010) *Pediatr Cardiol* 31(5): 598-606; Fraisse & Wessel (2010) *Pediatr Crit Care Med* 11(2 Suppl): S37-40; Taylor and Laussen (2010) *Pediatr Crit Care Med* 11(2 Suppl): S27-29; Bronicki & Chang (2011) *Crit Care Med* 39(8): 1974-1984; Fraisse et al. (2011) *Intensive Care Med* 37(3): 502-509; Checchia et al. (2012) *Pediatr Cardiol* 33(4): 493-505; Brunner et al. (2014) *Pulm Circ* 4(1): 10-24. The mainstay of current therapy remains inhaled nitric oxide (iNO). Nitric oxide, like most of the other therapies, is a reactive therapy that first requires a patient to develop the respiratory complications of cardiopulmonary bypass before therapy can be initiated. Moreover, inhaled nitric oxide has two main drawbacks; (A) inhaled nitric oxide has a marked rebound phenomenon when discontinued; and (B) when nitric oxide complexes with hemoglobin, it leads to methemoglobinemia. While phosphodiesterase 5 inhibitors such as sildenafil have been used to blunt the rebound of inhaled nitric oxide, the results have not been uniform.

Accordingly, there exists in the art a need for a more effective method for reducing the sequelae of CPB-induced pulmonary injury in a patient during surgery and postoperatively.

SUMMARY OF VARIOUS EMBODIMENTS OF THE INVENTION

The present invention provides a method for maintaining the coupling of endothelial nitric oxide synthase (eNOS) to reduce the incidence or severity of cardiopulmonary bypass-induced pulmonary injury due to free radical formation in a patient during cardiopulmonary bypass comprising administering an effective amount of citrulline to the patient. The effective amount of citrulline may be administered to the patient during or after the surgery. The effective amount of citrulline may be administered to the patient during and after the surgery. The effective amount of citrulline may be administered to the patient before, during, and after the surgery.

In many embodiments, the effective amount of citrulline may be an amount sufficient to reduce the uncoupling of endothelial nitric oxide synthase (eNOS). In many embodiments, the effective amount of citrulline may be an amount sufficient to reduce the formation of free radicals. In many embodiments, the effective amount of citrulline may be an amount sufficient to reduce the incidence or severity of cardiopulmonary bypass-induced pulmonary injury. In many embodiments, the citrulline may be administered to the patient prior to the surgery. In many embodiments, the citrulline may be administered at about 12 hours prior to the surgery. In many embodiments, the citrulline may be administered to the patient at the initiation of the surgery. In many embodiments, the citrulline may be administered to the patient during the surgery. In many embodiments, the citrulline may be administered to the patient after the surgery.

This method may be used when the surgery may be to correct a cardiac defect. This method may be used when the cardiac defect may be associated with excess pulmonary blood flow. In particular embodiments, the cardiac defect may be an atrial septal defect. In particular embodiments, the atrial septal defect may be a large arterial septal defect. In particular embodiments, the cardiac defect may be a ventricular septal defect. In particular embodiments, the ventricular septal defect may be a large unrestrictive ventricular septal defect (VSD). In particular embodiments, the cardiac defect may be a single ventricle lesion. In particular embodiments, the single ventricle lesion may be repaired by Glenn and Fontan procedures. In many embodiments, the cardiac defect may be Aortic Valve Stenosis (AVS), Atrial Septal Defect (ASD), Coarctation of the Aorta (CoA), Complete Atrioventricular Canal defect (CAVC), d-Transposition of the great arteries, Ebstein's Anomaly, I-transposition of the great arteries, Patent Ductus Arteriosis (PDA), Pulmonary Valve Stenosis, Single Ventricle Defects, Tetralogy of Fallot, Total Anomalous Pulmonary Venous Connection (TAPVC), Truncus Arteriosus, or Ventricular Septal Defect (VSD). In particular embodiments, the surgery may be arterial switch procedure. In particular embodiments, the cardiopulmonary bypass may be to repair a partial or complete atrioventricular septal defect (AVSD). In particular embodiments, the cardiopulmonary bypass may be to repair an ostium primum atrial septal defect (primum ASD).

The citrulline may be administered at the initiation of the surgery may be about 100-500 mg/kg of citrulline. Preferably, the bolus of citrulline at the initiation of the surgery may be about 100-300 mg/kg of citrulline. Preferably, the bolus of citrulline at the initiation of the surgery may be about 150 mg/kg of citrulline. Preferably, the citrulline is administered at the initiation of the surgery may be about 100, 150, 200, 250, 300, 350, 400, 450, or 500 mg/kg of citrulline. Preferably, the citrulline administered during the surgery may be added to the filtration. More preferably, the citrulline administered during the surgery may be added to hemoconcentration replacement fluid.

In many embodiments, the citrulline may be added at about 100-500 µmol/L. In many embodiments, the citrulline may be added at about 100-300 mol/L. In many embodiments, the citrulline may be added at about 100, 150, 200, 250, 300, 350, 400, 450, or 500 µmol/L. In many embodiments, the citrulline may be added at about 200 mol/L.

A citrulline bolus may be administered about 5-60 minutes after the surgery. In many embodiments, the citrulline bolus may be administered about 15-45 minutes after the surgery. In many embodiments, the citrulline bolus may be administered about 5, 10, 15, 20, 25, 30, 35, 40, 45, 50, 55, or 60 minutes after the surgery. In many embodiments, a citrulline bolus may be administered about 30 minutes after the surgery.

In many embodiments, the citrulline bolus may be about 5-50 mg/kg citrulline. In many embodiments, the citrulline bolus may be about 5, 10, 15, 20, 25, 30, 35, 40, 45, or 50 mg/kg citrulline. In particular embodiments, the citrulline bolus may be about 20 mg/kg citrulline.

The citrulline bolus may be administered about 30 minutes after cardio pulmonary bypass decannulation.

In many embodiments, citrulline may be administered to the patient for about 12-48 hours after surgery. In many embodiments, the citrulline may be administered to the patient for about 12, 24, 36, or 48 hours after surgery. In many embodiments, after surgery citrulline may be infused into the patient for about 48 hours. In many embodiments, the citrulline may be administered by infusion at about 3-12 mg/kg/hour. In many embodiments, the citrulline may be administered by infusion at about 3, 4, 5, 6, 7, 8, 9, 10, 11, or 12 mg/kg/hour. In many embodiments, the infusion may be about 9 mg/kg/hour.

In many embodiments, the citrulline may be administered intravenously. In many embodiments, the citrulline may be administered perioperatively. In many embodiments, a bolus of citrulline may be administered at the beginning of the surgical procedure.

In many embodiments, the citrulline may be administered orally, intravenously, by inhalation, or a combination thereof.

In many embodiments, the citrulline bolus may be about 150 mg/kg.

In many embodiments, the citrulline may be added at about 200 µmol/L to the filtration and hemoconcentration fluid utilized during the surgery.

In many embodiments, a bolus of about 20 mg/kg of citrulline may be administered after decannulation from cardiopulmonary bypass.

In many embodiments, after decannulation from cardiopulmonary bypass, a 9 mg/kg/hr continuous infusion of citrulline may be administered, optionally for about 48 hours.

In many embodiments, a bolus of 150 mg/kg of citrulline may be administered at the beginning of surgery followed 4 hours postoperatively by a continuous infusion of 9 mg/kg/hour of citrulline.

In many embodiments, the patient may have a T1405N genotype in the CPSI gene of CC, AC, AA, or a combination thereof. In particular embodiments, the patient may have a T1405N genotype in the CPSI gene of CC.

In many embodiments, the patient's plasma citrulline level may be raised above about 37, 50, 100, 150, or 200 µmol/L. In many embodiments, the patient's plasma citrulline level may be raised above about 37, 50, 100, 150, or 200 µmol/L postoperatively. In many embodiments, the patient's plasma citrulline level may be raised above about 100 µmol/L. In many embodiments, the patient's plasma citrulline level may be raised above about 100 µmol/L postoperatively. In many embodiments, the patient's plasma citrulline level may be raised to about 37-200 µmol/L postoperatively, preferably 100-200 µmol/L postoperatively. In many embodiments, the patient's plasma citrulline level may be raised to about 37 µmol/L to 2.5 mM. In many embodiments, the patient's plasma citrulline level may be raised to between about 37 µmol/L to 200 mol/L, 100 µmol/L to 1 mM/L, 150 µmol/L to 500 mol/L.

In a particular embodiment, the patient's plasma citrulline level may be raised for at least 12-48 hours postoperatively. In many embodiments, the patient's plasma citrulline level may be raised for over 48 hours postoperatively.

In particular embodiments, the patient may be a neonate, pre-adolescent, adolescent, or an adult. In many embodiments, the patient may be less than about 6 years old. In many embodiments, the patient may be less than about 10 days old. In many embodiments, the patient may be a preterm infant.

In many embodiments, patient's intensive care unit (ICU) stay may be decreased, preferably less than 27 days.

In many embodiments, the patient may be at risk for acute right-sided heart failure, tricuspid regurgitation, systemic hypotension, myocardial ischemia, and increased airway resistance.

In many embodiments, the patient may be at risk for persistent pulmonary hypertension of the newborn (PPHN).

In many embodiments, the effective amount of citrulline may be sufficient to prevent uncoupling of eNOS.

In many embodiments, the patient may be at risk for acute lung injury. In a particular embodiment, the patient may have acute lung injury.

In many embodiments, the patient may be at risk for postoperative pulmonary hypertension. In a particular embodiment, the patient may have postoperative pulmonary hypertension.

In many embodiments, the method may reduce the incidence of sequelae of cardiopulmonary bypass-induced pulmonary injury in patients during cardiopulmonary bypass surgery and postoperatively.

In many embodiments of the method of this invention, the method may reduce the severity of sequelae of cardiopulmonary bypass-induced pulmonary injury in patients during cardiopulmonary bypass surgery and postoperatively.

BRIEF DESCRIPTION OF THE DRAWINGS

FIG. 9A depicts the mean for Patients 6 and 8. FIG. 9B depicts the mean for Patients 9 and 10. FIG. 9C depicts the mean for Patients 13-16. The patients received a dose of citrulline (50, 100, or 150 mg/kg) preoperatively and postoperatively.

FIG. 11A depicts the decrease in mean citrulline levels in infants over 60 hours. FIG. 11B depicts the decrease in mean arginine levels in infants over 60 hours.

FIG. 18A depicts the systolic and diastolic blood pressure. No significant change in systolic and diastolic blood pressure of patients receiving citrulline. FIG. 18B depicts the mean arterial pressure of patients receiving citrulline (citrulline) versus those without citrulline (placebo). No significant change in the mean arterial pressure of patients receiving citrulline.

FIG. 25A the duration of post-operative mechanical ventilation for these patients was set to zero and all patients with ventilation time zero was censored. In FIG. 25B, patients with zero ventilation time was not censored. Both analyses, show statistically significant decrease in the time with invasive mechanical ventilation for patients receiving citrulline.

FIG. 28A have no additional censoring and FIG. 28B have zero censored. FIG. 28A-B show that patients receiving citrulline have a lower inotrope score than patients receiving a placebo.

FIG. 32A depicts all patients with no additional censoring. FIG. 32B depicts all patients re-intubation excluded and no additional censoring.

FIG. 33A depicts all patients re-intubation included and no additional censoring. FIG. 33B depicts all patients re-intubation excluded with no additional censoring. The composite value was censored if the duration of inotrope use was 48 hours and mechanical ventilation shorter than 48 hours.

DETAILED DESCRIPTION OF PREFERRED EMBODIMENTS

Figure 1:
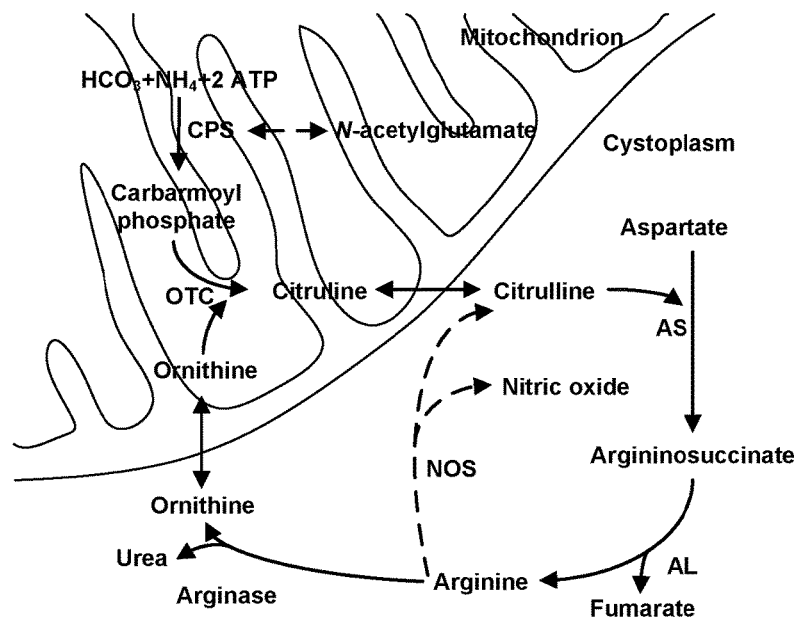
FIG. 1 depicts the hepatic urea cycle.
Figure 2:
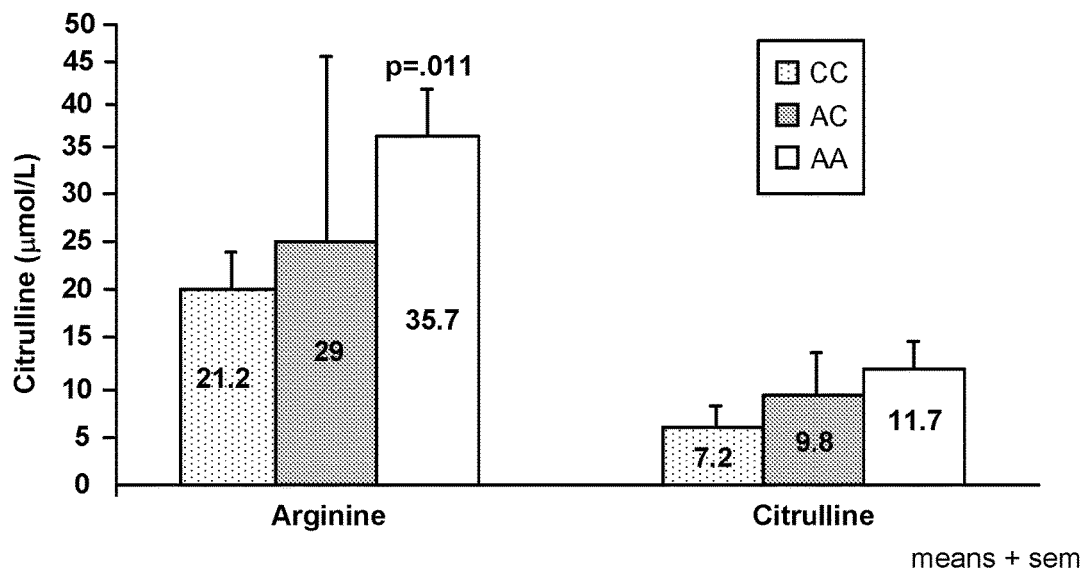
FIG. 2 depicts the effect of genotype of CPSI polymorphisms (CC, AC, and AA) on plasma arginine and citrulline levels. These are CPSI polymorphisms that result in the T1405N genotype.

The invention provides for reducing sequelae of cardiopulmonary bypass-induced pulmonary injury in patients during cardiopulmonary bypass surgery and postoperatively by maintaining plasma citrulline levels. A sustained perioperative plasma citrulline level >37 µmol/L for up to 48 hours postoperatively may be achieved by the methods described herein. Preferably, a sustained perioperative plasma citrulline level >100 µmol/L for up to 48 hours postoperatively may be achieved by the methods described herein. This will reduce the incidence and/or severity of sequelae of cardiopulmonary bypass-induced pulmonary injury in patients during cardiopulmonary bypass surgery and postoperatively.

The inventors surprisingly discovered that intravenous citrulline supplementation increases postoperative plasma arginine levels and prevents sequelae of cardiopulmonary bypass-induced pulmonary injury by reducing the uncoupling of eNOS. Reducing the incidence and/or severity of sequelae of cardiopulmonary bypass-induced pulmonary injury in patients during cardiopulmonary bypass surgery and postoperatively reduces costs and frees personnel and equipment for other uses. The methods described herein use intravenous citrulline for prevention of sequelae of cardiopulmonary bypass-induced pulmonary injury in pediatric patients undergoing surgery for congenital heart defects.

Cardiopulmonary bypass causes a systemic inflammatory response characterized clinically by acute compromise of cardiovascular and pulmonary function. Apostolakis et al. (2010) *Journal of Cardiac Surgery* 25(1): 47-55; Huffmyer & Groves (2015) "Pulmonary Complications of Cardiopulmonary Bypass." *Best Practice & Research Clinical Anesthesiology*. However, for a number of medical and physiological reasons, pediatric patients subjected to CPB during surgical repair of congenital heart defects are more susceptible to this cascade and at greater medical risk therefrom than adult patients. Kozik & Tweddell (2006) *The Annals of Thoracic Surgery* 81(6): S2347-S2354; Shekerdemian (2009) *Heart* 95(15): 1286-1296; Schure (2010) *Southern African Journal of Anesthesia and Analgesia* 16(1): 46-51. Reduction of key manifestations of acute CPB-induced lung injury, namely the post-operative need for mechanical ventilation and for inotrope therapy may be used to measure clinical effectiveness.

Oxidative Damage Due to Uncoupled eNOS

The inventor has observed that when a patient is subjected to cardiopulmonary bypass (CPB), a systemic inflammatory response is induced due to a drop in plasma citrulline levels. This drop in plasma citrulline leads to the uncoupling of eNOS and the production of radical oxygen species. The resultant oxidative damage leads to CPB-associated pulmonary injury.

Multiple observational and clinical studies have shown that plasma levels of citrulline and arginine drop precipitously and do not recover for up to 48 hours after cardiopulmonary bypass for congenital cardiac surgery. Due to intracellular transport mechanisms and intracellular processing, citrulline is the ultimate substrate for endogenous production of nitric oxide. Barr et al. (2003) *The Journal of Pediatrics* 142(1): 26-30; Smith et al. (2006) *The Journal of Thoracic and Cardiovascular Surgery* 132(1): 58-65; Barr et al. (2007) *The Journal of Thoracic and Cardiovascular Surgery* 134(2): 319-326.

Endothelial nitric oxide synthase (eNOS) is a dimer when fully functional, e.g., when converting arginine to nitric oxide (NO) and citrulline. Maintaining the dimer form of eNOS requires an effective level of citrulline. When citrulline falls below a threshold level, the eNOS dimer uncouples. The uncoupled eNOS still binds substrate, but produces free radicals, rather than NO. The free radicals contribute to the damage of inflammation, leading to the injury sequelae to cardiopulmonary bypass. Poor NO production by uncoupled eNOS leads to higher pulmonary vascular resistance, thereby promoting pulmonary hypertension.

The pathophysiology of pulmonary lung injury sequelae after repair of a variety of congenital heart defects involves a drop in the plasma citrulline levels (below, e.g., 37 mol/L) that in turns leads to an uncoupling of the eNOS enzyme. The uncoupled eNOS enzyme produces oxygen radicals that cause oxidative damage underlying the pulmonary lung injury that can be part of the sequelae after cardiopulmonary bypass. The Arginine Paradox is clinically significant, because arginine cannot serve in the role of preventing uncoupling of eNOS and consequent prevention of oxidative damage due to uncoupled eNOS.

The Arginine Paradox

Early studies using cell-free systems suggested that nitric oxide (NO) is produced from arginine. In the early 1990s, scientists believed that nitric oxide production was dependent on free arginine processed by the NO synthase enzyme. Citrulline was believed, at this time, to be a by-product of the process rather than a driver. In fact, at this time, citrulline was used as an indicator of NO production, as it was erroneously believed to be a byproduct of NO production. See e.g., Moncada & Higgs *N. Engl. J. Med.* 329 (27) 2002-2012 (1993) and Stamler, et al. *Science* 258 (5090) 1898-1902 (1992). This early understanding, however, was contrary to studies done under physiological conditions and published later, these later studies describe the "Arginine Paradox." The "Arginine Paradox" is manifested by an increase in NO production in the face of unchanged plasma arginine levels.

Studies show that the half-saturating arginine concentration for eNOS is less than 10 µM. It was also reported in journals that the intracellular arginine concentrations range from 0.1 to 0.8 mM in endothelial cell cultures. Accordingly, the active site of eNOS would expected to be saturated by the intracellular arginine in these cells, and increasing the extracellular arginine would not be expected to increase NO production. This observation was reported by Fike et al. *Am J Physiol Lung Cell Mol Physiol* 274: L517-L526 (1998).

However, in vitro and in vivo studies show that NO production by endothelial cells under physiological conditions can be increased by extracellular arginine, despite a saturating intracellular arginine concentration. On the other hand, the intracellular concentration of arginine in endothelial cells can be varied over 100-fold without changing nitric oxide (NO) production. This observation, i.e., that extracellular arginine administration drives NO production even when intracellular arginine is available in excess, is called the "Arginine Paradox." McDonald, et al. (1997) *The Journal of Biological Chemistry* 272(50): 31213-31216, 31213. Additionally, during this time it was found that exogenous arginine does not increase NO production in physiological systems. See, e.g., Blum, et al. *Circulation* 101(18): 2160-2164 (2000) and Chin-Dusting, et al. *J. Am. Coll. Cardiol:* 27(5): 1207-1213 (1996).

It is now understood that citrulline can stimulate nitric oxide (NO) production even in the presence of saturating levels of arginine. Further, extracellular citrulline does not influence intracellular arginine levels. Therefore, NO production actually depends on the use of urea cycle-produced or recycled citrulline entering the enzymatic complex with argininosuccinate and arginine as internal intermediates, and not an exogenous arginine supply. Dioguardi (2011) *J Nutrigenet Nutrigenomics* 4: 90-98. Accordingly, adequate plasma levels of citrulline will reduce the severity and incidence of sequelae of cardiopulmonary bypass-induced pulmonary injury.

Sequelae of Cardiopulmonary Bypass-Induced Pulmonary Injury

A number of factors place the lung at risk for injury during CPB. Chief among these is surface activation of neutrophils and other leukocytes, complement, and cytokines (pro- and anti-inflammatory) inter alia, and an associated systemic inflammatory cascade. Apostolakis et al. (2010) *Journal of Cardiac Surgery* 25(1): 47-55; Schure (2010) *Southern African Journal of Anesthesia and Analgesia* 16(1): 46-51. The degree to which the lung is damaged by the inflammatory response mediated by contact activation of leukocytes during extracorporeal circulation can vary in severity from microscopic changes of no clinical consequence to a capillary leak syndrome, or, in the worst case, to acute respiratory failure.

Pulmonary injury manifests in several ways and may involve both parenchymal and vascular lung tissues. Parenchymal effects of CPB are reflected in alterations in pulmonary compliance, most commonly related to an increase in lung water. The impact of this on the patient is a requirement for increased ventilatory support and a diminished ability of the lungs to perform their function in gas exchange. Vascular effects are manifested by changes in pulmonary vascular resistance, which in turn affect the function of the right ventricle. This condition constitutes in effect, pulmonary arterial hypertension. The lungs are in a unique position in the circulation and may thus be vulnerable to different mechanisms of injury. Circulating leukocytes that elaborate inflammatory mediators following contact with surfaces in CPB apparatus or by direct damage by CPB equipment account for only part of the inflammatory damage that may occur in the lung. Clark (2006) *Perfusion* 21(4): 225-228. The lung is also an important source of inflammatory cells as well as being a target for damage by those same cells. The consequences of the mechanical and inflammatory effects on the lung is decreased functional residual capacity, diminished compliance, and impaired gas exchange. These changes are ultimately associated with increased pulmonary vascular resistance and pulmonary artery pressure.

Acute CPB-induced lung injury leads to significant cardiopulmonary problems. The inflammatory response leads to constriction of the pulmonary and systemic vasculature. The constriction leads to increased right ventricular and left ventricular workload. The inflammatory response also leads to pulmonary edema and deterioration in lung compliance and postoperative lung function. The standard treatments for these postoperative complications include mechanical ventilation until the lung function returns to normal and inotropic support until pulmonary and systemic vascular tone returns to normal, eventually decreasing the right and left ventricular workload. Mechanical ventilation and inotropic support are therapies that can thus serve as effective biomarkers of acute CPB-induced lung injury. Additionally, prolonged mechanical ventilation can in turn often lead to other morbidities including ventilator associated lung injury, ventilator associated pneumonia (VAP), central line associated blood stream infections (CLABSI), and even more prolonged intensive care unit stays. Prevention of sequelae of cardiopulmonary bypass-induced pulmonary injury is therefore a desirable therapeutic goal.

Pediatric CHD Patients

Children undergoing surgery for congenital heart defects are especially susceptible to developing CPB-induced acute lung injury due to age dependent differences in the inflammatory response, and the elevated sensitivity of their immature organ systems to injury as well as distinct differences between pediatric and adult CPB. Kozik & Tweddell (2006) *The Annals of Thoracic Surgery* 81(6): S2347-S2354. Neonates and infants are especially affected as the relatively large extracorporeal circuit size, the blood prime and the need for increased flow rates result in greater exposure of blood to the foreign surface. Schure (2010) *Southern African Journal of Anesthesia and Analgesia* 16(1): 46-51.

For congenital cardiac surgery, the extracorporeal circuit must be adjusted to a wide range of age groups and size variations, from 1.5 kg premature infants to >100 kg adolescents or adults. Infants and children have smaller circulating blood volumes, higher oxygen consumption rates and, often, highly reactive pulmonary vascular beds. In addition, neonates and infants have labile thermoregulation and immature organ systems with multiple implications for ischemic tolerance and inflammatory response. Many complex repairs require a bloodless operative field, which can be difficult to achieve in the presence of intra or extra cardiac shunts, aortopulmonary collaterals, or otherwise increased pulmonary venous return. Schure (2010) *Southern African Journal of Anesthesia and Analgesia* 16(1): 46-51.

The differences between adult and pediatric CPB are shown in Table 1.

TABLE 1

Tabular overview of differences between adult and pediatric CPB (Schure 2010)

| Parameter | Adult Patient | Pediatric patient |
| --- | --- | --- |
| Estimated blood volume | 65 ml/kg<br>(4-5 liters for 70 kg) | <10 kg: 85 ml/kg<br>(285 ml for 3 kg) |
| Dilution effects on blood volume | 25-33% | 100-200% |
| Addition of whole blood or packed red blood cells to prime | Rarely | Usually |
| Oxygen consumption | 2-3 ml/kg/min | 6-8 ml/kg/min |
| Full CPB flow | 50-75 ml/kg/min | 150-200 ml/kg/min for <3 kg |
| Minimum CPB temperature | Rarely <25-32° C. | Commonly 15-20° C. |
| Use of total circulatory arrest or regional low flow perfusion | Rare | Common |
| Perfusion pressures | 50-80 mmHg | 20-50 mmHg |
| Acid-base management | Mainly Alpha-stat | Alpha-stat and/or pH-stat |
| Measured PaCO2 | 30-45 mmHg | 20-80 mmHg |
| Glucose-regulation | | |
| hypoglycaemia | Rare (major hepatic injury); | Common, reduced stores |
| hyperglycaemia | Common, treated with Insulin | Less common, risk for rebound hypoglycaemia |

The functional and structural status of the pulmonary vascular bed plays a pivotal role in the presentation and outcome of children with congenital cardiovascular disease. However, it is in the immediate postoperative period that these pediatric patients are most vulnerable to sequelae of cardiopulmonary bypass-induced pulmonary injury. Sequelae of cardiopulmonary bypass-induced pulmonary injury represents a complex interplay between the preoperative condition of the patient (importantly age at repair, type of lesion, and presence of a syndrome) and the inevitable disruption in the endocrine and vasoactive peptide milieu that results from cardiac surgery. Important factors leading to enhanced vasoconstriction are cardiopulmonary bypass, hypothermia, and circulatory arrest with some degree of associated ischemia. Residual cardiac lesions and the sequelae of the stress response, hypoxia, metabolic, and respiratory acidosis may all contribute additional imbalances that favor pulmonary vasoconstriction. Many of the manifestations of acute lung injury associated with CPB can be explained wholly or in part by endothelial dysfunction, which provides at once a possible unifying hypothesis as well as a potential therapeutic target. Acute lung injury associated with CPB may also lead to important adverse cardiac sequelae. The inflammatory response after surgery for CHD is commonly associated with abnormal ventricular-vascular interaction, with systemic vasoconstriction and elevated afterload, as well as with myocardial injury with impaired systolic and diastolic function. In a proportion of patients, these haemodynamic manifestations can lead to the serious consequence of low cardiac output. Shekerdemian (2009) *Heart* 95(15): 1286-1296.

The serious sequelae of pulmonary injury are clinically important to outcome. These sequelae are risk factors for prolonged intensive care stay, and death. Lability of pulmonary vascular tone is common in neonates and infants after surgery for CHD. This can be most problematic after biventricular repairs in patients who had preoperative unrestricted pulmonary flow (large septal defects, common arterial trunk) or pulmonary venous hypertension (obstructed anomalous pulmonary venous drainage). Instability of the pulmonary vascular resistance is also common after palliative surgery in patients with a functionally univentricular circulation, including Norwood-type operations, a systemic-to-pulmonary artery shunt, or a pulmonary artery band. While many therapeutic interventions optimize systemic oxygen delivery through their direct influences on the myocardium and systemic vasculature, manipulation of the pulmonary vascular tone can play an important role in optimizing the circulation of children undergoing surgery for heart disease. Shekerdemian (2009) *Heart* 95(15): 1286-1296.

Citrulline, with its mechanism of action, is intended as a preventive treatment to reduce the risk of the development of the sequelae of cardiopulmonary bypass-induced pulmonary injury and thus to positively influence the postoperative recovery of pediatric patients undergoing surgery for congenital heart defects.

The cardiac defects, including congenital cardiac defects, include but are not limited to cardiac defects associated with excess pulmonary blood flow. The cardiac defect may be an atrial septal defect, for example a large arterial septal defect. The cardiac defect may be a ventricular septal defect, for example, a large unrestrictive ventricular septal defect (VSD). The cardiac defect may be a single ventricle lesion. The single ventricle lesion may be repaired by Glenn and Fontan procedures. The cardiac defect may be an Aortic Valve Stenosis (AVS), Atrial Septal Defect (ASD), Coarctation of the Aorta (CoA), Complete Atrioventricular Canal defect (CAVC), d-Transposition of the great arteries, Ebstein's Anomaly, I-transposition of the great arteries, Patent Ductus Arteriosis (PDA), Pulmonary Valve Stenosis, Single Ventricle Defects, Tetralogy of Fallot, Total Anomalous Pulmonary Venous Connection (TAPVC), Truncus Arteriosus, or Ventricular Septal Defect (VSD). The patient may be a neonate, a juvenile, an adolescent, or an adult.

Citrulline and Arginine are Different in Mechanism and Effect

Arginine and citrulline are both products of the urea cycle, but at different stages of the cycle. In nitrogen clearing cells, arginine is processed by arginase to urea, while in cells producing nitric oxide, arginine is processed by nitric oxide synthase (NOS) to produce nitric oxide and citrulline. Extracellular arginine is ineffective in generating a significant increase in stimulated or unstimulated nitric oxide production in vascular endothelial cells. See also Surdacki, et al. *Wien Klin Wochenschr*. (1994) 106(16): 521-6. In contrast, citrulline is a potent stimulator of NO production.

Figure 23:
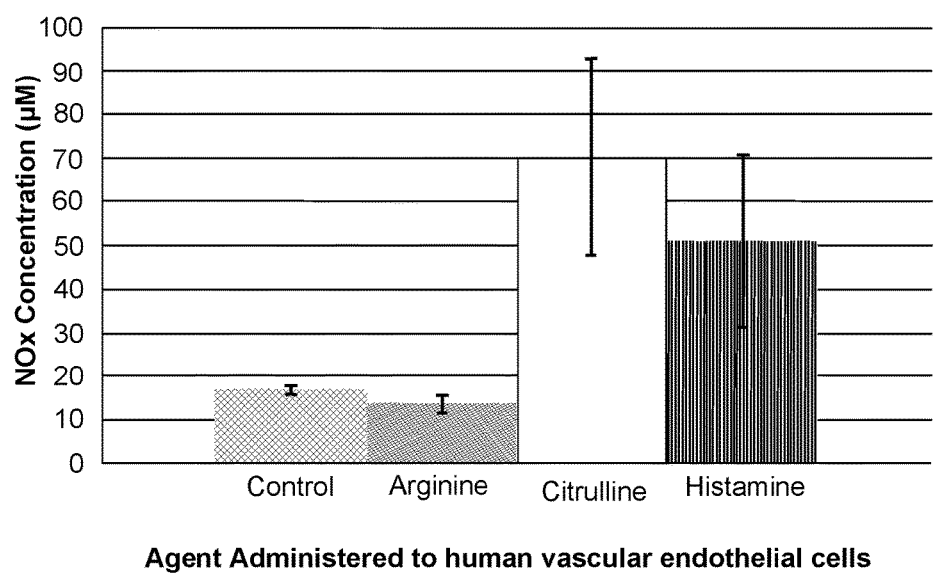
FIG. 23 depicts a comparison of nitric oxide (NO) production in endothelial cells by arginine, citrulline, and histamine. Arginine is not equivalent to citrulline in NO Production

FIG. 23 shows an experiment measuring the production of nitric oxide by human vascular endothelial cells exposed to no agent (negative control), arginine, citrulline, and histamine (positive control). These agents were administered to cultured human vascular endothelial cells stimulated with acetylcholine. Measurement of nitric oxide was through a Seiver's system of nitrate/nitrites. The experiment clearly demonstrates that arginine has no effect on the production of nitric oxide by the human vascular endothelial cells. Arginine directly applied to an endothelial cell generates little sign of increased NO production, even with very high concentrations (10 mM). On the other hand, extracellular addition of citrulline to endothelial cells increases the production of NO by these cells. Furthermore, the inventors found that blocking transport of citrulline (through the SNAT1 transporter) significantly reduces nitric oxide production under normal and hypoxic conditions.

This observation is in part due to the complexing of the enzymes involved, creating a substrate tunnel that can only be entered by citrulline. Beyond the substrate channeling, there is also poor transport of arginine into cells. This is the underlying principal of the Arginine Paradox in which arginine fails as a direct effector of nitric oxide production in a whole cell system. See, e.g., Summar et al., *Mol. Genet. Metab.* 2004; 81 Suppl 1:S12-9.

Under physiological conditions, citrulline can stimulate nitric oxide (NO) production even in the presence of saturating levels of arginine. Further, extracellular citrulline does not influence intracellular arginine levels. Therefore, NO production actually depends on the use of urea cycle produced or recycled citrulline entering the enzymatic complex with argininosuccinate and arginine as internal intermediates, and not on an exogenous arginine supply. Dioguardi (2011) *J Nutrigenet Nutrigenomics* 4: 90-98.

Arginine and citrulline molecules differ, for example, in the production of nitric oxide. There is no evidence or reason to believe that citrulline can substitute for all of the roles of arginine in the body, including roles such as de novo protein production. Arginine and citrulline are not biological equivalents.

Arginine is the substrate of nitric oxide synthase (NOS) for generating nitric oxide (NO) with citrulline as a byproduct. The citrulline is recycled back to arginine by arginiosuccinic synthetase (ASS) and arginiosuccinic lysase (ASL), constituting the citrulline-NO cycle. The arginine is produced in situ by the enzymes of this cycle, and extracellular and exogenous sources of arginine do not replenish an arginine deficiency. See, e.g., Erez, et al. (2011) *Nature Medicine* 17(12): 1619-1626. Further, eNOS forms an enzyme dimer which requires sufficient arginine to remain in the (active) dimer form. As noted by Erez, citrulline is required for the in situ production of arginine, and exogenous sources of arginine are insufficient to provide arginine required by NOS for NO production. When the arginine levels drop, as during hypoxia, the dimer uncouples and begins producing free radical oxygen and peroxynitrites. It has been demonstrated that high levels of circulating citrulline provide some protection against oxidative damage in tissues. See, e.g., Grisafi et al. *Lung* (2012) 190(4): 419-30.

The inventors found that exogenous arginine in physiological systems does not increase NO production. See, e.g., Chin-Dusting, et al. *J. Am. Coll. Cardiol*: 27(5): 1207-1213 (1996). When the arginine levels drop, as during cardiopulmonary surgery and the post-operative period thereafter, the NOS dimer, i.e., enzyme, uncouples and begins producing free radical oxygen radicals ($O^{\bullet}$). Additionally, superoxide production might increase from enzymatic sources other than eNOS, such as NADPH oxidase. Liu, et al. *Am J Physiol Lung Cell Mol Physiol* (2006) 290: L2-L10. This excess superoxide production might have directly interacted with NO to reduce its local production. Here, the maintaining adequate plasma levels of citrulline allows for enough NO production to maintain the eNOS enzyme as a dimer and preventing the production of oxygen radicals.

Citrulline May be Inadvertently Removed by Hemofiltration and Dialysis

In a large prospective observational study of children undergoing congenital cardiac surgery, plasma citrulline and arginine levels were significantly decreased after surgery and did not return to preoperative baseline levels for up to 48 hours.

Increased pulmonary vascular tone (PVT) can be an important perioperative issue in children undergoing congenital cardiac surgery, even for patients not thought preoperatively to be at significant risk for severe pulmonary artery hypertension. Clinical safety and pharmacokinetic studies were conducted that show both oral and intravenous citrulline to be well tolerated and without adverse side effects in infants and children undergoing repair of congenital heart defects. A subsequent small randomized placebo controlled trial of citrulline revealed that citrulline was well tolerated with no adverse events; however, in some patients significant citrulline removal occurred during hemofiltration and dialysis performed during cardiopulmonary bypass. In previous studies of potential genetic risk factors for increased PVT, it was noted that the genotype of an important polymorphism in the key urea cycle enzyme carbamyl phosphate synthetase 1 (CPSI T1405N) affects the risk of elevated pulmonary vascular tone in infants and children undergoing surgical repair of congenital heart defects and in neonates at risk for postoperative pulmonary hypertension (PPHN). In addition it was noted that all patients, regardless of polymorphism genotype had a significant decline in plasma levels of key urea cycle intermediates including citrulline and arginine. These associations prompted the inventors to investigate perioperative supplementation with citrulline.

Initial supplementation trials utilized oral citrulline at a dose of 1.9 g/kg before cardiopulmonary bypass, immediately postoperatively and every 12 hours, continuing for 48 hours after surgery. Oral citrulline was well tolerated with no evidence of significant adverse events (such as systemic hypotension). In addition it was noted that patients who had a 12 hour plasma citrulline level >37 umol/L (the upper range of normal levels) did not develop increased PVT.

Unfortunately not all patients receiving oral citrulline reached these levels. These findings helped in the design of subsequent studies with intravenous citrulline. In a dose escalation study targeting a sustained plasma level of around 100 mol/L, the inventors noted that intravenous citrulline has a fairly short half-life. To address this problem, the inventors developed a combination bolus and continuous infusion drug delivery protocol. The combined protocol of a bolus of 150 mg/kg at the beginning of surgery, followed postoperatively 4 hours later with a continuous infusion of 9 mg/kg/hr, resulted in an sustained plasma citrulline levels of approximately 100 mol/L. No adverse side effects were noted.

At Vanderbilt, 77 patients have been treated with this protocol. The study was stopped in preparation for a larger multicenter randomized placebo controlled trial. The analysis of the data from these 77 patients revealed that a majority who received citrulline did not reach the therapeutic sustained target plasma citrulline level of about 100 mol/L, primarily due to a previously unknown removal of citrulline by filtration and hemoconcentration occurring during cardiopulmonary bypass.

Citrulline and Cardiopulmonary Bypass

Intravenous perioperative citrulline supplementation increases postoperative plasma arginine levels and avoids uncoupling of eNOS, leading to a decrease in the sequelae of cardiopulmonary bypass induced injury. The inventors developed an improved protocol for maintaining pulmonary vascular tone during and after surgery which comprises administration of an intravenous citrulline bolus of 150 mg/kg at the initiation of cardiopulmonary bypass (CPB), the addition of L-citrulline at a concentration of 200 µmol/L to the filtration or hemoconcentration replacement fluid utilized during cardiopulmonary bypass, a citrulline bolus of 20 mg/kg 30 minutes after CPB decannulation, immediately followed by the start of a 9 mg/kg/hr continuous infusion for 48 hours. Inhaled nitric oxide (NO), like most of the other therapies, is a reactive therapy that first requires a patient to develop the respiratory complications of cardiopulmonary bypass before therapy can be initiated. This stands in marked contrast to citrulline, which appears to prevent the onset of the sequelae of cardiopulmonary bypass-induced pulmonary injury.

This revised protocol is designed to maintain a sustained therapeutic plasma citrulline level above the target threshold of about 100-200 µmol/L from the initiation of cardiopulmonary bypass, throughout surgery, and for up to about 48 hours after surgery. Separate IV access is not required for citrulline. The citrulline formulation is isotonic and can run through either a peripheral IV or a central venous catheter. Citrulline is an amino acid and thus for compatibility purposes may be treated like parental nutrition. Additionally, citrulline is compatible with fluids used for filtration or hemoconcentration during cardiopulmonary bypass.

Figure 3:
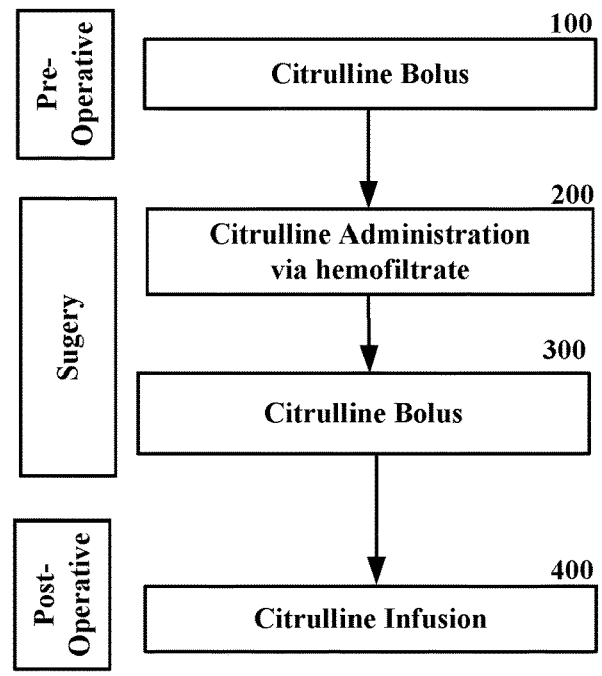
FIG. 3 depicts a flow-chart of an exemplary protocol for the treatment of sequelae of CPB-induced pulmonary injury in a patient during surgery and postoperatively.

Referring to FIG. 3, an exemplary flow chart shows a method of maintaining adequate plasma citrulline levels comprising administering citrulline to a patient during and after surgery.

With reference to FIG. 3, during pre-operative stage, a citrulline bolus of 150 mg/kg may be administered to the patient 100. During surgery, citrulline may be administered at a concentration of 200 µmol/L to the filtration or hemoconcentration replacement fluid utilized during surgery 200. During post-operative stage, a citrulline bolus of 20 mg/kg may be administered 300 and may be followed by a 9 mg/kg/hr continuous infusion for 48 hours 400.

Citrulline Formulations

Citrulline (2-amino-5-(carbamoylamino)pentanoic acid) [$C_6H_{13}N_3O_3$] is an amino acid. Citrulline solution for IV administration may be manufactured by methods known in the art. See, e.g., Kakimoto, et al. (1971) *Appl Microbiol* 22(6): 992-999.

Methods of Use

The citrulline may be administered before a surgical procedure. The suitable dosing may include an intravenous citrulline bolus of 150 mg/kg at the initiation of cardiopulmonary bypass. Citrulline may be administered during a surgical procedure. A suitable dosing may be the addition of citrulline at a concentration of 200 µmol/L to the filtration and hemoconcentration fluid utilized during cardiopulmonary bypass. Citrulline may be administered after a surgical procedure. A bolus of 20 mg/kg of citrulline 30 minutes after decannulation from cardiopulmonary bypass, immediately followed by a 9 mg/kg/hr continuous infusion for 48 hours. The methods described herein may be used to maintain a patient's citrulline plasma level above about 37 µmol/L. The filtration or hemoconcentration replacement fluid may be provided as standard fluid, e.g., Plasmalyte® (sterile, non-pyrogenic isotonic solution), with citrulline added to achieve a citrulline concentration of 200 mol/L. Doses may be given by a central intravenous catheter that will be placed after induction of anesthesia or via the bypass circuit.

Citrulline may be infused into a patient by an intravenous route to maintain a plasma citrulline level. A protocol for maintaining an adequate supply of plasma citrulline during surgery may comprise administration of an intravenous citrulline bolus (e.g., 150 mg/kg) at the initiation of cardiopulmonary bypass (CPB), the addition of citrulline (e.g., at a concentration of 200 mol/L) to the filtration or hemoconcentration replacement fluid utilized during surgery, optionally cardiopulmonary bypass, a citrulline bolus (e.g., 20 mg/kg) 30 minutes after CPB decannulation, immediately followed by the start of a continuous infusion (e.g., 9 mg/kg/hr) for 48 hours.

The intravenous citrulline bolus at the initiation of cardiopulmonary bypass (CPB) may be about 100-300 mg/kg. The intravenous citrulline bolus at the initiation of cardiopulmonary bypass (CPB) may be about 100, 125, 150, 175, 200, 225, 250, 275, or 300 mg/kg. In a preferred mode, the intravenous citrulline bolus at the initiation of cardiopulmonary bypass (CPB) may be about 150 mg/kg.

Citrulline may be added at a concentration of about 100-300 µmol/L to the filtration or hemoconcentration replacement fluid utilized during surgery, optionally including cardiopulmonary bypass. Citrulline may be added at a concentration of about 100, 125, 150, 175, 200, 225, 250, 275, or 300 µmol/L to the filtration or hemoconcentration replacement fluid utilized during surgery, optionally during cardiopulmonary bypass. In a preferred mode, the citrulline may be added at a concentration of about 200 µmol/L to the filtration or hemoconcentration replacement fluid utilized during surgery, optionally during cardiopulmonary bypass. For example, any fluids added or removed during the surgery must be taken into consideration in order to maintain a concentration of about 200 µmol/L citrulline throughout the course of the surgery.

The citrulline bolus administered 30 minutes after decannulation, typically after cardiopulmonary bypass, may be about 10-30 mg/kg. A citrulline bolus of about 10, 15, 20, 25, or 30 mg/kg may be administered shortly after the conclusion of cardiopulmonary bypass, typically about 30 minutes after decannulation. In a preferred mode, a citrulline bolus of about 20 mg/kg may be administered typically 30 minutes after decannulation, following cardiopulmonary bypass.

The continuous infusion may be at about 5-15 mg/kg/hour citrulline about 5, 6, 7, 8, 9, 10, 11, 12, 13, 14, or 15 mg/kg/hour citrulline. The continuous infusion may be at about 9 mg/kg/hour citrulline.

Citrulline may be administered orally at a dosage of about 5-15 g/kg, i.e., about 5, 6, 7, 8, 9, 10, 11, 12, 13, 14, or 15 g/kg of citrulline. The oral dosage of citrulline may be about 9 g/kg of citrulline.

The target level for plasma citrulline may be maintained at about 37 µmol/L to 2.5 mM. For example, the plasma citrulline level of the patient may be maintained above about 37, 40, 45, 50, 75, 100, 125, 150, 175, 200, 225, 250, or 300 µmol/L. The plasma citrulline level of the patient may be maintained above about 37, 100, or 200 µmol/L. The methods described herein may be used to maintain a patient's citrulline plasma level between about 37 µmol/L to 200 µmol/L, 100 µmol/L to 1 mM/L, 150 µmol/L to 500 µmol/L citrulline.

The citrulline may be provided in dose unit form. For example, the citrulline may be provided in a container containing 300 mg sterile citrulline formulated for injection. This may be reconstituted for use using 6 mL sterile water and further diluted with approximately 5.9 mL sterile NaCl solution 0.9% Ph. Eur. to a total volume of 12 mL and a concentration of 300 mg/12 mL (i.e., 25 mg/mL). The citrulline may be formulated for injection at a concentration of 10-40 mg/mL, for example 10, 15, 20, 21, 22, 23, 24, 25, 26, 27, 28, 29, 30, 35, or 40 mg/mL. The citrulline may be provided as a drug product at 500 mg sterile citrulline for injection in 10 mL of sterile water. This may be used to infuse patients using sodium chloride 0.9% Ph. Eur.

In one embodiment, on the day of the surgery the patient is administered a bolus of 150 mg/kg citrulline, adding citrulline at 200 µmol/L to the filtration and hemoconcentration fluids. About 30 minutes post-surgery, a bolus of 20 mg/kg citrulline is administered and a continuous intravenous infusion of citrulline at 9 mg/kg/hour is started after the bolus (e.g., within 5-10 minutes, preferably immediately following the administration of the bolus) and maintained for 6-48 hours, preferably for 48 hours.

For example, an L-citrulline bolus of 150 mg/kg can be administered at the initiation of cardiopulmonary bypass (CPB) with citrulline at a concentration of 200 µmol/L added to the filtration and hemoconcentration fluid utilized during CPB; a bolus of 20 mg/kg of L-citrulline can be administered 30 minutes after decannulation from CPB, immediately followed by a 9 mg/kg/hr continuous infusion of L-citrulline for 48 hours. Doses can be administered by a central IV catheter that may be emplaced after induction of anesthesia or via the bypass circuit. Separate IV access is not required for this drug administration. Citrulline is isotonic and can run through either a peripheral IV or a central venous catheter. Citrulline (L-Citrulline) is an amino acid, and thus, for compatibility purposes, the drug product is treated like parenteral nutrition. Additionally, it is compatible with fluids used for filtration or hemoconcentration during CPB.

Postoperative Parameters

The clinical outcome of patients treated with intravenous citrulline may be assessed by: the necessity and length of postoperative mechanical ventilation, incidence of increased postoperative PVT by echocardiograms, serum creatinine and liver enzyme levels, Inotrope score, length and volume of chest tube drainage, length of ICU stay, length of hospitalization, and/or survival rate.

Postoperative Mechanical Ventilation:

The duration of postoperative invasive mechanical ventilation is the time in hours from separation from cardiopulmonary bypass until endotracheal extubation. A decrease in the time spent on postoperative invasive mechanical ventilation is a positive postoperative outcome.

Incidence of Increased Postoperative PVT by Echocardiograms:

Increased PVT is defined as a right ventricular (RV) pressure >½ systemic arterial pressure. If postoperative PVT remains unchanged, as compared to a control group, this is a positive postoperative outcome.

Serum Creatinine & Liver Enzymes:

Serum electrolyte, creatinine, and CBC Levels may be recorded daily from admission to PCCU until PCCU discharge. Additionally, liver enzymes may be obtained during the baseline, 24 hour, and 28 day/discharge periods. If serum electrolyte, creatinine, and CBC Levels are comparable to a control group, this would be a positive postoperative outcome.

Inotrope Score:

The inotrope dose should be monitored post operatively from the time of PCCU admission using the following scoring system:

Dopamine (mcg/kg/min)×1
plus Dobutamine (mcg/kg/min)×1
plus Milrinone (mcg/kg/min)×10
plus Epinephrine (Adrenaline) (mcg/kg/min)×100
plus Phenylephrine (mcg/kg/min)×100
plus Norepinephrine (Noradrenaline) (mcg/kg/min)×100
=total inotrope score See, e.g., Hoffman, et al. *Circulation* (2003) 107: 996-1002. A decrease in the inotrope score would be a positive postoperative outcome.

Duration of Chest Tube Usage:

The total postoperative length in hours and total volume of chest tube drainage in cc prior to discontinuation of the chest tubes by the surgical team may be recorded. A decrease in the postoperative length of time and/or total volume of chest tube drainage, as compared to a comparison group, would be a positive postoperative outcome.

Length of Intensive Care Unit (ICU) Stay:

Length of ICU stay may be calculated in two ways: (1) as total number of postoperative days spent in an ICU or ICU step down bed until the patient has been cleared by the physician team to be ready for transfer to a non-ICU area; and (2) as total number of hours postoperative that the patient required either mechanical ventilator or continuous intravenous inotrope or vasodilator support. A decrease in the length of ICU stay by either of these measures would be a positive postoperative outcome.

Length of Hospitalization:

Length of hospitalization may be calculated as the total number of days postoperative until discharge from the hospital. A decrease in the length of hospitalization would be a positive postoperative outcome.

Survival:

Both 28 day postoperative survival and survival to discharge home from the hospital may be recorded. Increased survival after 28 days postoperative would be a positive postoperative outcome.

Hemodynamic Improvement:

Hemodynamic data including heart rate, systemic arterial blood pressure, $O_2Sat$, CVP, and PAP may be monitored as an indicator of the severity or incidence of cardiopulmonary bypass-induced pulmonary injury as a consequence of uncoupling of eNOS due to a drop in plasma citrulline levels.

Additionally, hemodynamic improvement and postoperative pulmonary vascular tone (PVT) may be used as indicators of an improvement in the patient's condition, e.g., decreasing the severity or incidence of cardiopulmonary bypass-induced pulmonary injury as a consequence of uncoupling of eNOS due to a drop in plasma citrulline levels. Lipid perodixation end-products and protein carbonyl groups may be used as measures of oxidative damage. Further, hydrogen peroxide in bodily fluids, including urine, may also be used to detect oxidative damage. See, e.g., Halliwell & Whiteman *British Journal of Pharmacology* (2004) 142: 231-255.

The inventors surprisingly discovered that intravenous citrulline delivery mitigates sequelae of cardiopulmonary bypass-induced pulmonary injury, as evidenced by the reduction of post-operative need for mechanical ventilation and inotrope therapy in pediatric subjects undergoing repair of congenital heart defects.

For example, the duration of mechanical ventilation was reduced, the duration of the use of inotropes to support cardiac output was reduced, the duration of treatment with concomitant vasoactive medication was shorter, and overall need for respiratory support was lower in patients receiving citrulline as compared to patients receiving a placebo. Patients who received citrulline in accordance with the methods described herein exhibited shorter composite durations of positive pressure ventilation and inotrope therapy than patients receiving a placebo. Patients receiving citrulline in accordance with the methods described herein were ready for discharge from an Intensive Care Unit (ICU) sooner than patients receiving a placebo. Further, the overall hospital stay duration was shorter in citrulline-treated patients as compared to placebo-treated patients.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in surgery, biochemistry, medicine, physiology, and/or related fields are intended to be within the scope of the following claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The examples contained herein are offered by way of illustration and not by any way of limitation.

EXAMPLES

Example 1

Arginine, Citrulline, and Plasma Nitrate Levels and Risk of PPHN

Figure 4:
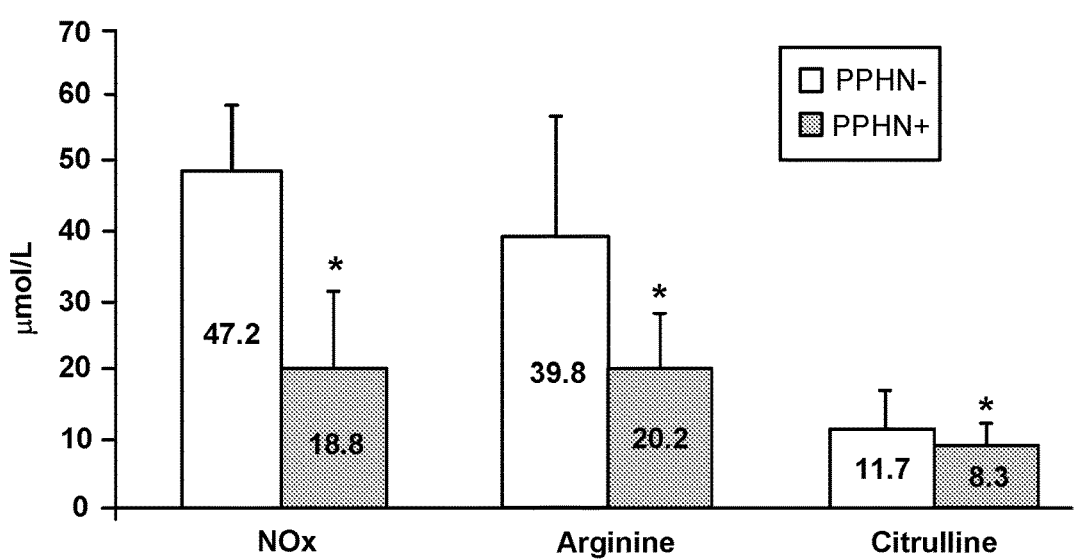
FIG. 4 depicts the reduction of NO and NO precursors, arginine and citrulline, in patients with persistent pulmonary hypertension in the newborn (PPHN).

Neonates who developed PPHN had lower arginine, citrulline, and plasma nitrate levels as compared to infants without PPHN. Ten neonates had plasma NO metabolites (NOx) measured using the modified Griess reaction; 5 were PPHN+ and 5 were PPHN−. The PPHN+ cases had a significantly lower mean level of NOx, (p=0.006) (FIG. 4). The neonates with PPHN had significantly lower plasma arginine and citrulline levels on amino acid analysis (FIG. 4). There were no significant differences in the levels of any other individual amino acids between the two groups. The number of subjects was too small to evaluate relationships between NOx and amino acid levels and genotype. This data shows that infants with PPHN have decreased urea cycle intermediates and products.

Example 2

Urea Cycle Function in Infants and Children Undergoing Cardiopulmonary Bypass for Correction of Congenital Heart Defects The prevalence of increased postoperative pulmonary vascular tone and status of urea cycle function in infants and children undergoing cardiac surgery was studied. Over a 20-month period, 169 infants and children who required one of the 6 specific surgical procedures for correction of their congenital heart defects were prospectively studied. See Table 1. After parental consent, all patients had blood drawn for genotype before surgery and blood collected for amino acid analysis at 5 different time points (pre-op, immediately postoperative, 12 hours, 24 hours and 48 hours postoperative). All patients, except those undergoing a Stage I Norwood, were monitored for increased postoperative pulmonary vascular tone (PVT+) defined as a mean PA pressure >20 mmHg. Infants undergoing a Stage I Norwood were defined as PVT+ if they had a clinical requirement for inhaled NO utilized for arterial saturations <60% with adequate systemic pressures.

Table 2 shows the average age for each of the six procedures and the length of cardiopulmonary bypass exposure. Of 169 patients, 56 (33.1%) developed clinical evidence of increased postoperative pulmonary vascular tone (PVT+). Many of these patients required clinical intervention including sedation, paralysis, and hyperventilation. Thirty-three patients were treated with inhaled NO (NO+).

TABLE 2

Type of Surgical Procedure Performed in Study Population

| Procedure | # | Age (mos) | CPB (min) | PVT+ | NO+ |
|---|---|---|---|---|---|
| Bidir Glenn Shunt | 42 | 6.4 ± 2.5 | 84 ± 36 | 18 (42.9%) | 10 (23.8%) |
| Norwood Stage I | 33 | 0.8 ± 0.8 | 112 ± 32 | 14 (42.4%) | 9 (27.3%) |
| VSD closure | 36 | 8.5 + 11.9 | 91 + 21 | 15 (41.7%) | 1 (2.8%) |
| AVSD repair | 24 | 5.2 + 2.5 | 111 + 27 | 12 (50%) | 3 (12.5%) |
| Arterial Switch | 18 | 0.6 + 1.3 | 157 + 38 | 6 (33.3%) | 2 (11.1%) |
| Modified Fontan | 16 | 24.8 + 18.8 | 94 + 25 | 4 (25%) | 3 (18.8%) |
| Total # of patients | 169 | 6.8 ± 10.6 | 104 ± 37 | 56 (33.1%) | 33 (19.5%) |

Infants and children undergoing cardiac surgery showed an increased postoperative pulmonary vascular tone and status of urea cycle function.

Effect of Cardiopulmonary Bypass on Urea Cycle Function

Figure 5:
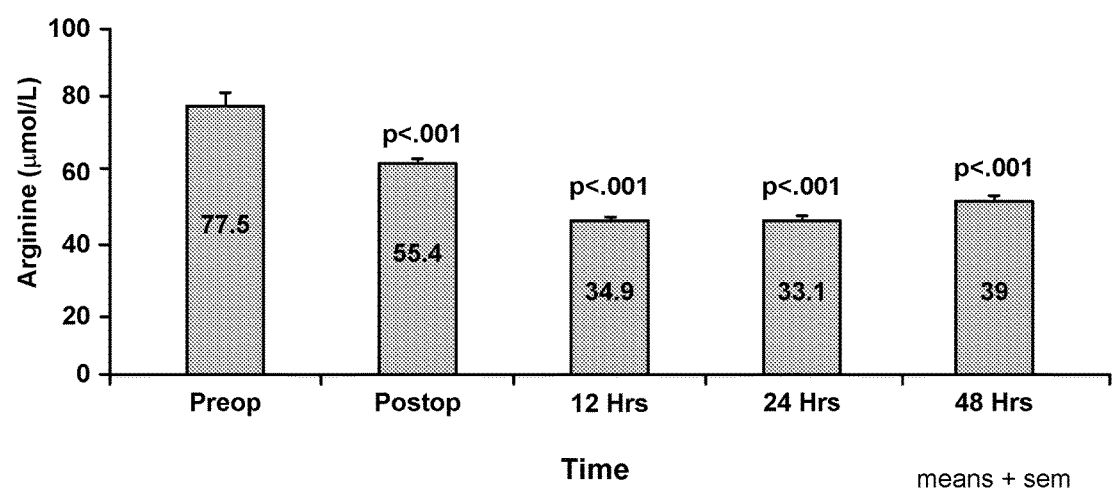
FIG. 5 depicts the reduction of plasma arginine levels from cardiopulmonary bypass (CP bypass). CP Bypass reduces a patient's plasma arginine levels.
Figure 6A:
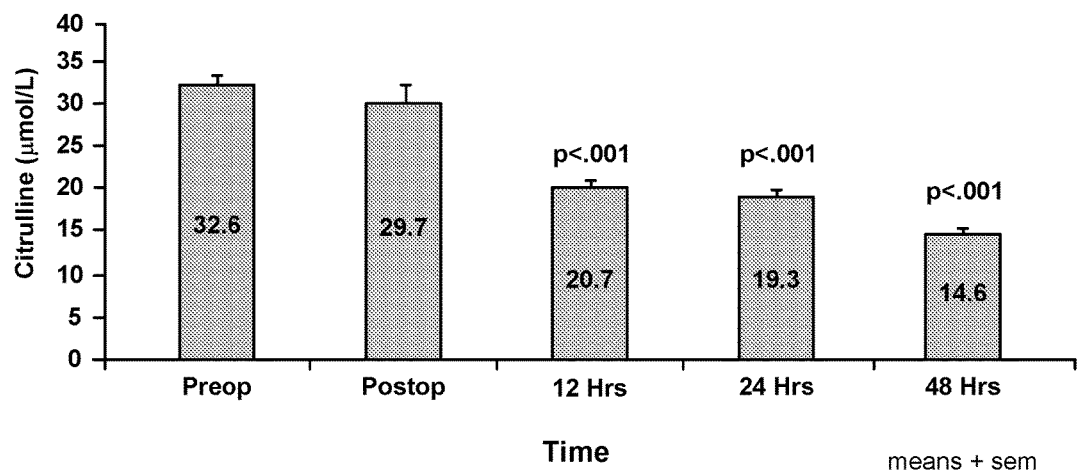
FIG. 6A-B depicts the reduction of plasma (FIG. 6A) and serum (FIG. 6B) citrulline levels from cardiopulmonary bypass. CP bypass reduces a patient's plasma and serum citrulline levels.
Figure 6B:
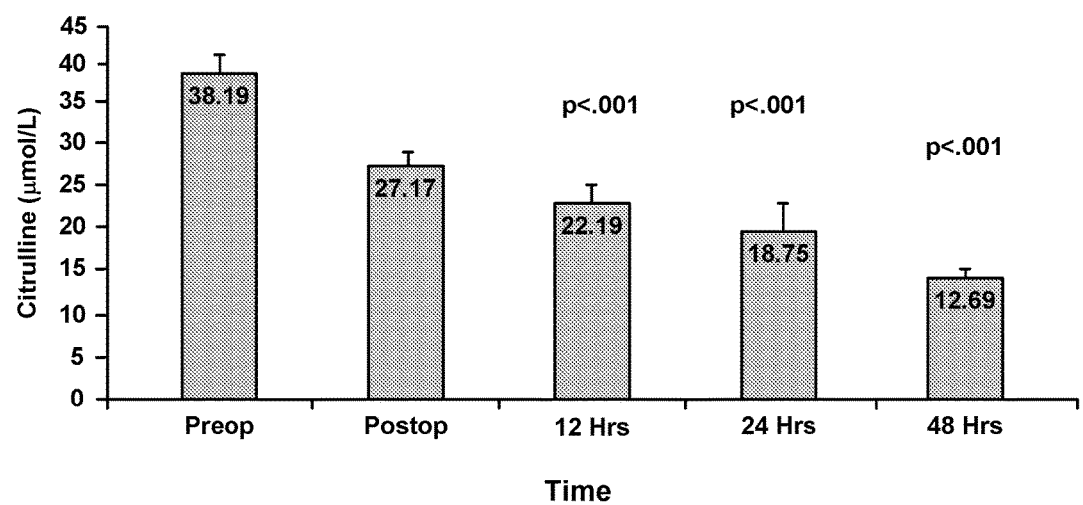
Figure 7:
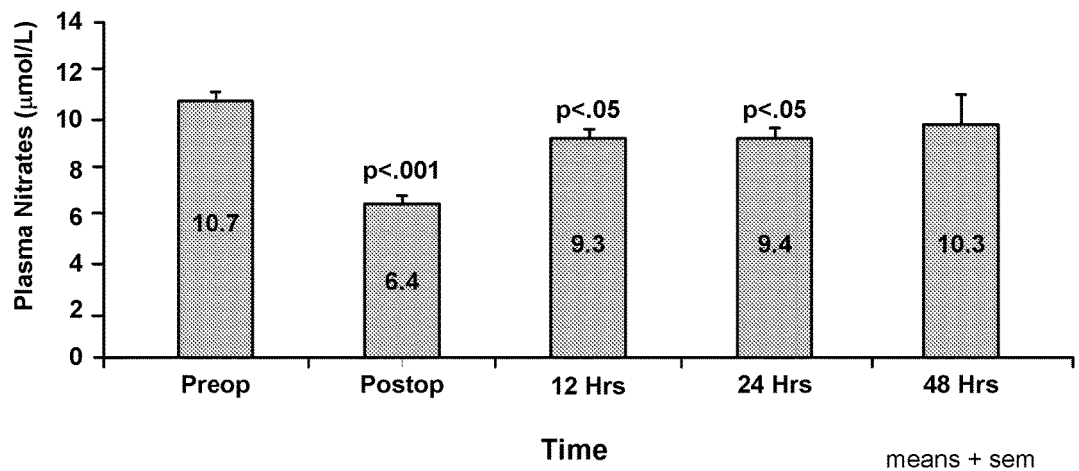
FIG. 7 depicts the reduction of plasma nitric oxide (NO) levels from cardiopulmonary bypass. CP bypass reduces the plasma NO levels.

To test whether a cardiopulmonary bypass would decrease urea cycle function and NO availability, perioperative urea cycle intermediates and plasma nitric oxide metabolites were analyzed. Plasma samples were collected from each of the 169 patients at 5 perioperative time points and were analyzed by cation exchange chromatography using a Beckmann 7300 amino acid analyzer (Beckmann, Palo Alto, Calif.). Arginine and citrulline were used as the primary markers of urea cycle flux. Plasma nitric oxide metabolite levels were used as an indirect measure of NO availability utilizing a colorimetric assay with modified Griess reagents and read at 540 nm absorbance. All patients required cardiopulmonary bypass for correction of their cardiac defects. Within the study population, cardiopulmonary bypass caused a significant decrease in mean arginine levels at all postoperative time points compared to preoperative levels (FIG. 5). A similar decrease was seen in mean citrulline levels (FIG. 6A-B). Plasma NO metabolite levels were also depressed immediately after surgery but showed a partial rebound at 12 and 24 hours before returning to preoperative levels at 48 hours (FIG. 7). In contrast, there was no effect of bypass on total amino acids not involved in the urea cycle. Because amino acids not involved in the urea cycle were not affected, this data suggests that the effect on urea cycle function and NO substrate synthesis may last for up to about 48 hours after surgery.

Figure 8:
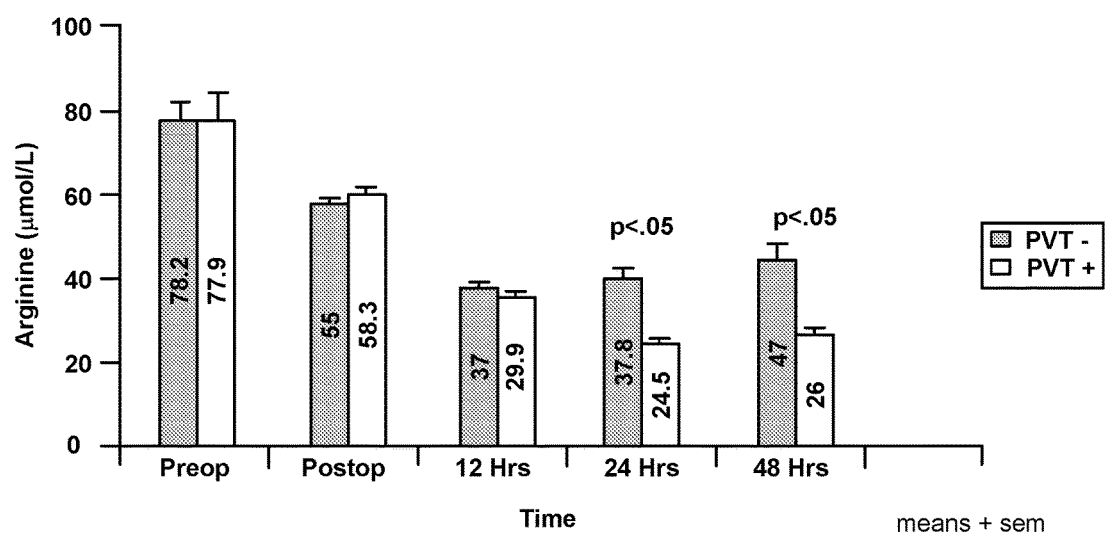
FIG. 8 depicts the reduction of arginine levels in patients with and without increased pulmonary vascular tone (PVT– and PVT+) preoperatively, postoperatively, and 12, 24, and 48 hours postoperatively.

In patients who subsequently developed increased postoperative PVT (PVT+), a decrease in plasma arginine levels was noted compared to patients without increased PVT (PVT−). FIG. 8. Similar observations were not noted for citrulline and NO metabolites.

Using linear regression, the length of cardiopulmonary bypass did not show any affect on plasma citrulline, and arginine, NO metabolite levels at any of the postoperative time points.

Summary of Clinical Results

This study shows cardiopulmonary bypass used for correction of congenital heart defects causes a significant decrease in urea cycle function with a large decrease in availability of precursors for nitric oxide synthesis. Cardiopulmonary bypass used for surgical correction of congenital heart defects caused a fairly significant decrease in availability of nitric oxide precursors in the urea cycle and nitric oxide levels measured indirectly by plasma NO metabolites. Because amino acids not involved in the urea cycle were not affected, an effect on urea cycle function and NO substrate synthesis may last up to 48 hours after surgery. Patients with increased postoperative pulmonary vascular tone had a more significant decrease in arginine levels than those with normal tone.

A separate study showed the risk of increased postoperative pulmonary vascular tone was influenced by CPSI T1405N genotype. Arginine levels were significantly different among CPSI T1405N genotypes at 48 hours after surgery.

Example 3

Intravenous Citrulline Supplementation Increases Plasma Arginine Levels

The objective was to assess the safety of intravenous citrulline and its effect on serum arginine levels in piglets. A total of 9 Duroc swine, aged 5-21 days, with a target minimum weight of 4 kg were utilized. All piglets underwent anesthetic induction and tracheostomy. Central lines were placed in the femoral artery and femoral vein and hemodynamics monitored continuously. Citrulline (600 mg/kg IV) was administered to 5 piglets. Saline was given to control animals. Serum amino acids were drawn before and each hour after citrulline administration.

Serum arginine levels peaked at 1-2 hours following intravenous citrulline administration and remained sustained above baseline three hours following, reaching significance at all time points compared to controls ($p<0.001$). No hemodynamic instability was observed. See Tables 3-4.

TABLE 3

Arginine Levels (μmol/L) Following intravenous citrulline

| Treatment Group (n = 5) | Baseline | 1 hour post | 2 hours post | 3 hours post |
|---|---|---|---|---|
| L-Citrulline (600 mg/kg) | 131.5 | 535.0 | 559.8 | 498.4 |
| Control (saline) | 89.6 | 103.0 | 118.1 | 136.7 |
| p-value | 0.1582 | <0.001 | <0.001 | <0.001 |

TABLE 4

Mean Arterial Blood Pressures (mmHg) Following intravenous Citrulline

| Treatment Group (n = 4) | Pre-dose | 1 hour post | 2 hours post | 3 hours post |
|---|---|---|---|---|
| L-Citrulline (600 mg/kg) | 67.0 | 67.4 | 64.8 | 62.2 |
| Control (saline) | 53.2 | 58.7 | 55.7 | 54.7 |

$p > .05$ at all time points

Therefore, intravenous administration of citrulline leads to sustained increase in plasma citrulline and arginine levels.

This would be beneficial in preventing the development of sequelae cardiopulmonary bypass-induced pulmonary injury.

Example 4

Perioperative Oral Citrulline Supplementation in Children Undergoing Congenital Cardiac Surgery The purpose of this study was to assess absorption and demonstrate safety of oral citrulline as a potential alternative to IV citrulline. 40 patients with one of the 5 surgical diagnoses identified above were randomized to receive 5 doses of oral citrulline (1.9 grams/kg) vs. placebo. The first dose was administered immediately prior to surgery and the second dose immediately on arrival in the Pediatric ICU after surgery followed every 12 hours×3 doses. Plasma citrulline levels were significantly higher in the citrulline group (36 vs. 26 mol/L, p=0.013) demonstrating adequate absorption.

TABLE 5

Serum Levels 12 hours postoperative with and without PHTN

| Serum Citrulline level 12 hours postop | No PHTN | +PHTN |
|---|---|---|
| <37 µmol/L | 18 patients | 9 patients |
| >37 µmol/L | 12 patients | 0 patients | p value = 0.036 (Fisher's exact)

The study was not adequately powered to detect an effect on the incidence of postoperative pulmonary hypertension (PHTN), however, patients with a plasma citrulline level >37 µmol//L did not develop pulmonary hypertension. This would be beneficial in preventing the development of sequelae cardiopulmonary bypass-induced pulmonary injury.

Example 5

Administration of Citrulline During Surgery

The initial goal was to test the safety and pharmacokinetics of three doses of intravenous citrulline in children undergoing surgical repair of specific congenital heart defects. Intravenous citrulline administration had a theoretical risk of systemic arterial hypotension. An adverse drop in mean arterial pressure was defined as a greater than a twenty percent decrease from baseline. The baseline postoperative mean arterial blood pressure was calculated as the average of mean arterial blood pressure measurements collected every 5 minutes for the 30 minutes immediately preceding the administration of the postoperative dose or infusion. The bedside monitor was then set to alarm if that 20% drop was reached at any time in the 48 hour study period.

Figure 9A:
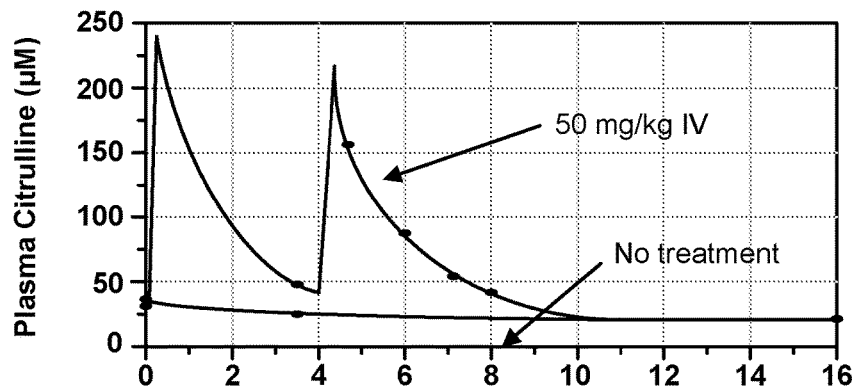
FIG. 9A-C depicts the citrulline plasma levels in patients with and without administration of a bolus of citrulline.
Figure 9B:
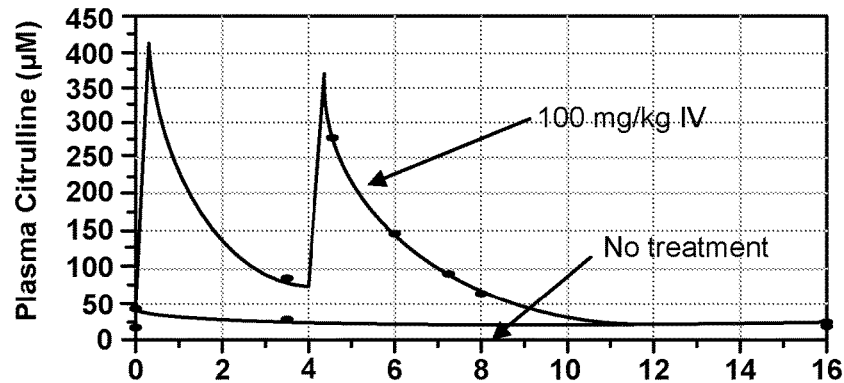
Figure 9C:
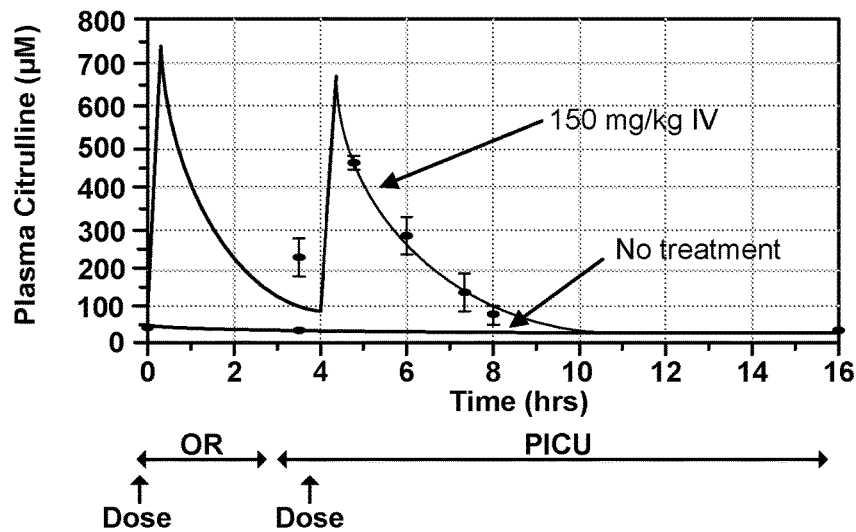

The original doses selected were 200, 400, and 600 mg/kg based on data from previous animal studies. The original study design was a 4 arm study using the 3 doses and a placebo control. Five patients were enrolled and the Data Safety and Monitoring Board (DSMB monitor promptly noted that the plasma levels achieved with these doses were very high although no adverse effects were noted. Subsequently the study design was changed to an open label dose escalation trial starting at 50 mg/kg and escalated the dose in 50 mg/kg intervals. Each patient received 2 doses, 1 dose in the operating room after initiation of cardiopulmonary bypass and one 4 hours later in the intensive care unit. The data is summarized in FIGS. 9A-C.

Figures 10A, 10B:
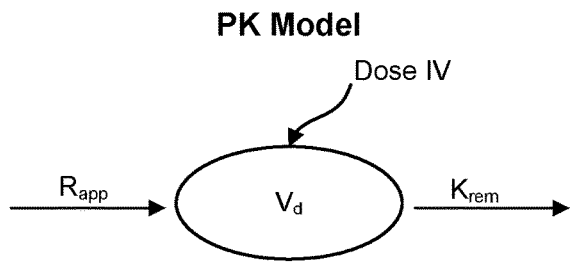
FIG. 10A-B depicts a PK model (FIG. 10A) and PK parameters (FIG. 10B).

Patients 6 and 8 received 50 mg/kg of intravenous citrulline and had a peak citrulline level of approximately 220 µmol/L and a 4 hour trough level of 40 µmol/L. No adverse side effects were noted. This trough was below the target range of 80-100 µmol/L and the dose was subsequently increased. Patients 9 & 10 received 100 mg/kg of intravenous citrulline and had a peak citrulline level of 375 µmol/L and a 4 hour trough of 50 µmol/L. Again, no adverse side effects were noted. This trough was also below the target range of 80-100 µmol/L and the dose was subsequently increased. Patient 13-16 received 150 mg/kg of intravenous citrulline and had a peak citrulline level of 660 µmol/L and a 4 hour trough of 80 µmol/L. This 4 hour trough was in the target range of 80-100 µmol/L and the dose was not escalated further. The pharmacokinetic profile of these 3 doses of citrulline is summarized in FIG. 10.

Figure 11A:
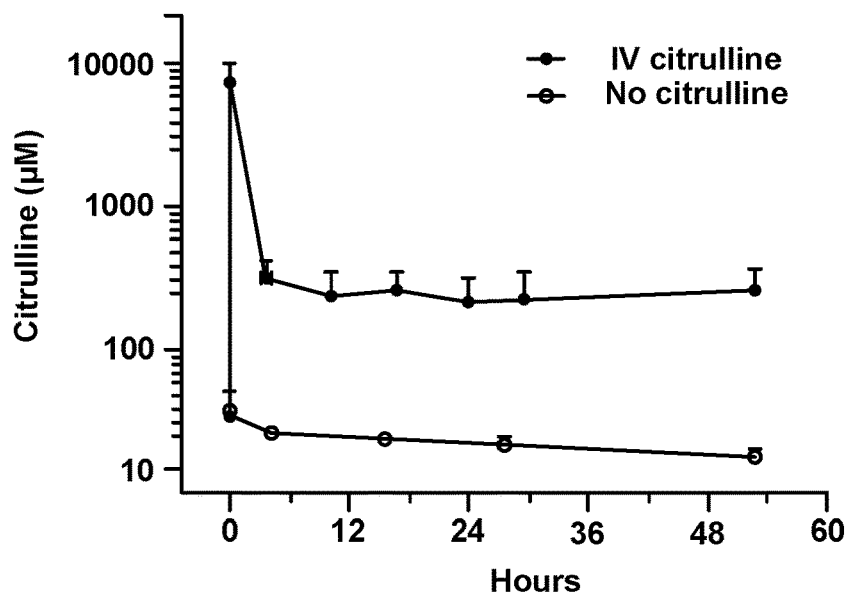
FIG. 11A-B depicts the mean citrulline and arginine levels in infants with and without the administration of intravenous citrulline ("IV citrulline") over 60 hours.
Figure 11B:
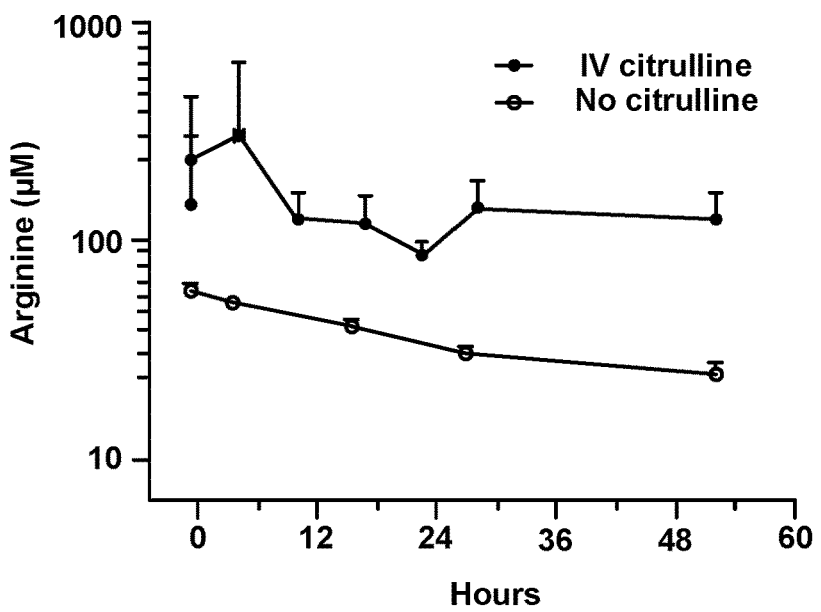

The half-life was calculated to be approximately 85 minutes which was too short to proceed with intermittent dosing. After pharmacokinetic modeling, the study design was changed to a bolus dose of 150 mg/kg given in the OR on cardiopulmonary bypass followed 4 hours later by a continuous infusion of 9 mg/kg/hour for 48 hours. Another 9 patients were enrolled. The mean plasma levels of both citrulline and arginine in study patients (+IV citrulline) compared to patients in the observational cohort (−IV citrulline) are depicted in FIGS. 11A-B.

There was one significant adverse event but it was not related to the use of IV citrulline. The patient developed a bradycardic arrest approximately 8 hours after an AVSD repair that was not preceded by systemic hypotension. The patient required emergent ECMO support for 48 hours and subsequently fully recovered and was discharged home on hospital day 22. The DSMB reviewed the case and determined that the significant adverse event was unlikely to be related to the citrulline administration.

Based on this data, it was determined that intravenous citrulline was safe and that the combination of a bolus of 150 mg/kg given on cardiopulmonary bypass at the beginning of surgery followed 4 hours later by a continuous infusion of 9 mg/kg/hr may maintain the pulmonary vascular tone postoperatively and an adequate supply of plasma citrulline.

Example 6

Figure 12:
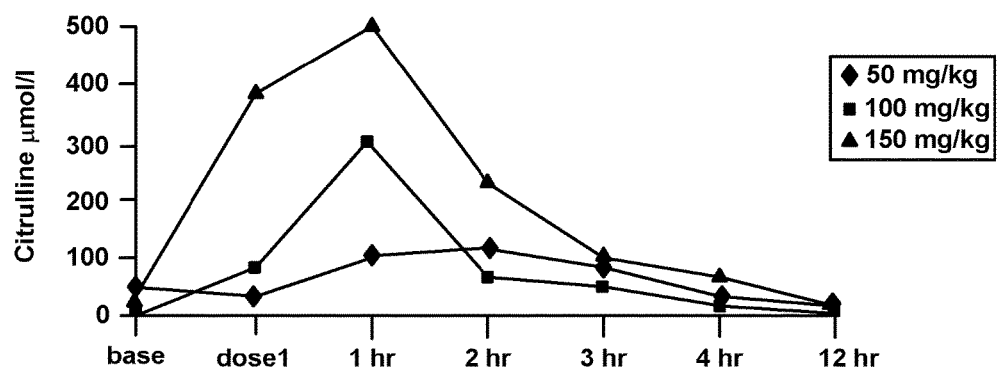
FIG. 12 depicts the plasma citrulline levels in patients administered a dose of citrulline (50, 100, or 150 mg/kg) postoperatively over 12 hours.

Perioperative Intravenous L-Citrulline Pharmacokinetics in Children Undergoing Congenital Cardiac Surgery To determine clearance of a single bolus dose of IV citrulline and optimal dose frequency, a dose escalation design using three concentrations of IV citrulline: 50, 100, & 150 mg/kg was utilized. The dose of citrulline was given in the operating room immediately after cannulation and initiation of cardiopulmonary bypass. The overall goal was to achieve a sustained citrulline level of 100 µmol/L or more up to four hours after the initial dose. The four hour time point was selected to allow for the surgical procedure to be completed and the patient to return to the Intensive Care Unit (ICU) postoperatively before further dosing. The composite citrulline data is shown in FIG. 12.

From this data it was determined that 150 mg/kg was the optimal dose as it resulted in four hour levels close 100 mol/L. There were no adverse effects including hypotension from administration of any of the concentrations of IV citrulline.

Figure 13:
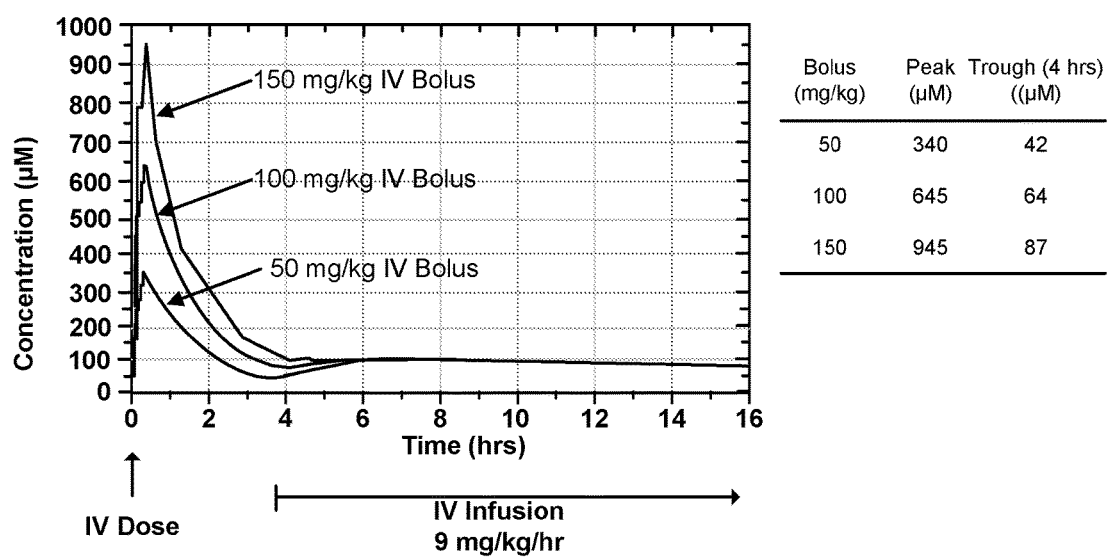
FIG. 13 depicts the plasma citrulline levels in patients administered a dose of citrulline (50, 100, or 150 mg/kg) postoperatively combined with an intravenous infusion of citrulline (9 mg/kg/hour) over 16 hours.

However, from the data above it was also determined that the ½ life of the bolus doses of IV citrulline was approximately 60-90 minutes and would require at least 4 hour dosing which is impractical even in an ICU setting. The pharmacokinetic modeling suggested a sustained citrulline level of approximately 100 µmol/L could be achieved by a bolus dose of 150 mg/kg of IV citrulline given at the beginning of surgery after initiation of cardiopulmonary bypass followed 4 hours later by a continuous infusion of 9 mg/kg/hr. The PK modeling of this regimen is shown in FIG. 13.

Figure 14A:
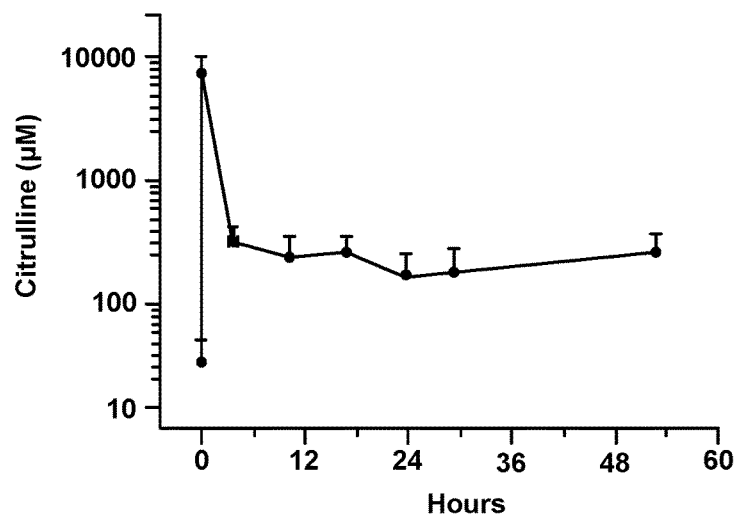
FIG. 14A-B depicts the mean citrulline levels in infants over 60 hours (FIG. 14A) and the mean citrulline levels of nine individual infants over 60 hours (FIG. 14B).
Figure 14B:
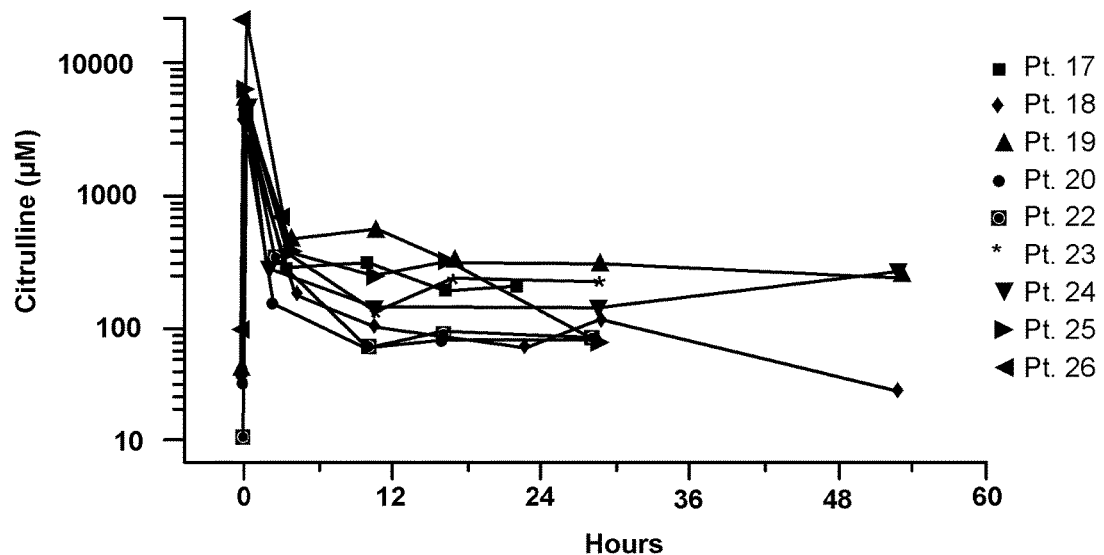

Patients were then enrolled using this revised protocol of a combination of a bolus dose of 150 mg/kg in the OR on CPB and a continuous infusion of 9 mg/kg/hr started postop in the PICU at 4 hours after the initial bolus dose. Citrulline data is available from 9 patients and are presented in FIGS. 14A-B. This shows the maintenance of an adequate supply of plasma citrulline.

Example 7

Intravenous Citrulline Study

An intravenous citrulline study conducted was a randomized, placebo controlled, double blind study with the primary clinical outcome being length of mechanical ventilation postoperatively and secondarily the incidence of postoperative pulmonary hypertension between the 2 treatment groups (citrulline vs placebo).

A total of 77 patients were enrolled at Vanderbilt Children's Hospital. Patients were screened based on the surgical schedule. Based on this schedule, patients undergoing one of the 5 planned cardiac surgeries included in this study were screened (patients undergoing the Norwood procedure are now excluded at the recommendation of the DSMB).

The study was stopped in preparation for a larger multi-center randomized placebo controlled trial. The analysis of the data from these 77 patients revealed that a majority who received citrulline did not reach the therapeutic sustained target plasma citrulline level of 100 µmol/L primarily due to removal of citrulline by hemofiltration occurring during cardiopulmonary bypass. These hemofiltration techniques had changed during the study, and the investigators were not aware of these changes.

Example 8

Protocol for Administration of Citrulline for Cardiac Surgery

The original pharmacokinetic model presumed a closed system. In the absence of significant metabolism and urine output during surgery, the model presumed that the therapeutic levels achieved by the original citrulline bolus would be maintained for the duration of surgery. However, at an unknown point early in the course of the study, perfusion practice changed to incorporate aggressive ultrafiltration and crystalloid exchange throughout surgery. This meant that the ultrafiltration effectively removed the citrulline from the circulation such that upon review of citrulline levels, virtually no patients had achieved therapeutic drug levels.

The study in this example was undertaken to test a revised dosing protocol designed to achieve and maintain therapeutic citrulline levels in the face of ultrafiltration and crystalloid replacement. While this pharmacokinetic endpoint was apparently achieved, the focus of this data presentation is upon the efficacy parameters that were assessed as secondary endpoints. The study recruited 22 patients randomized in equal numbers of 11 patients each to placebo and citrulline arms.

Results

Figure 15:
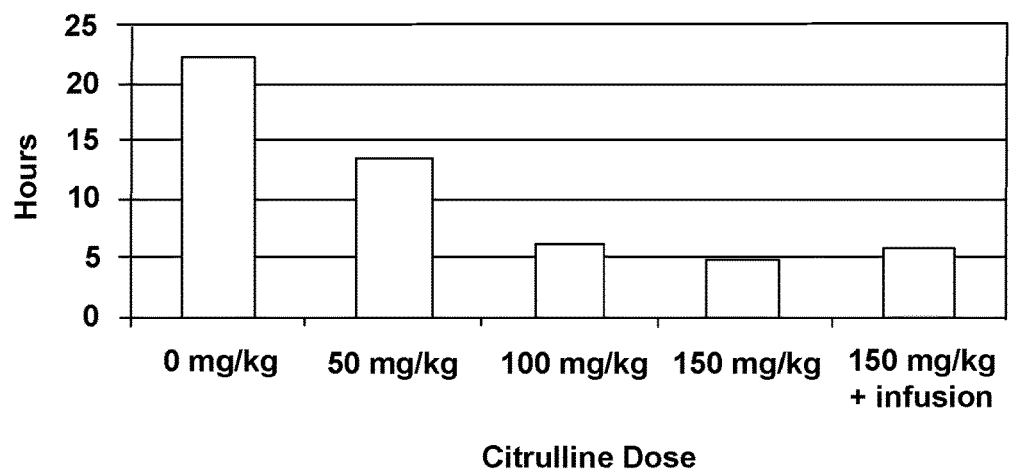
FIG. 15 depicts the length of postoperative ventilation with different doses of citrulline.
Figure 16:
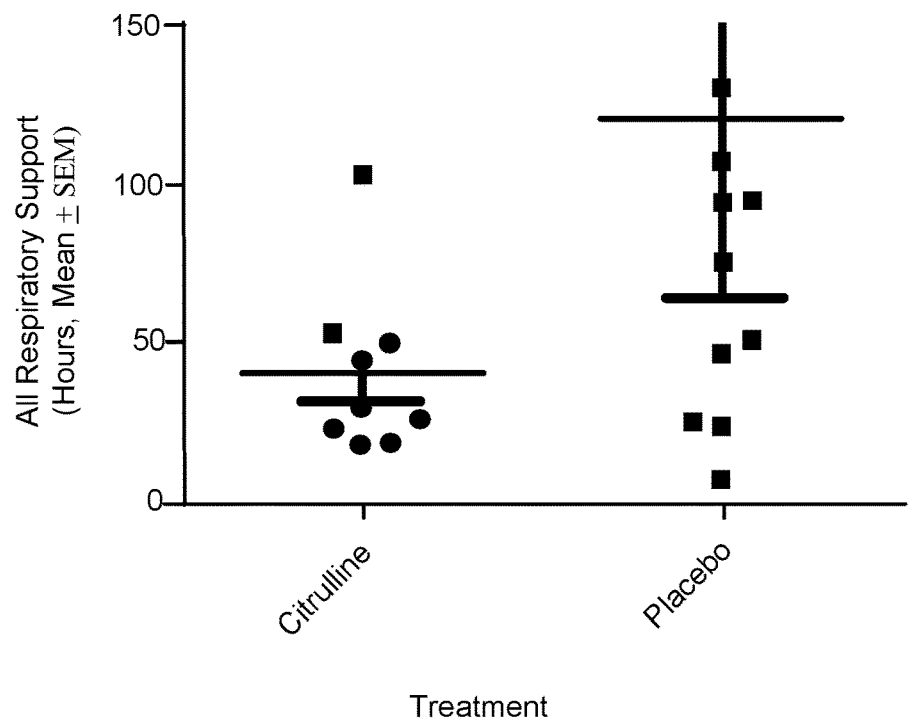
FIG. 16 depicts the effect of citrulline on respiratory outcome in congenital heart repair surgery. NB: a single data point is outside axis limits (placebo, 672 hours). P=0.1911 Satterhwaite t test, n=20 useable patients.

Early in the course of the study, it was recognized that one of the two participating centers routinely extubated all patients in the operating room immediately following cessation of cardiopulmonary bypass. This precluded use of the duration of mechanical ventilation as an endpoint. Instead, a post-hoc analysis was applied using the duration of all forms of ventilatory support as a possible endpoint. FIG. 15 shows the placebo control group to have a roughly bimodal distribution of ventilator times, with some children remaining on respiratory support for extended periods of time. In contrast, the citrulline-treated children, with the exception of one outlier, showed a unimodal distribution with reduced durations of respiratory support. The differences between placebo and citrulline groups did not achieve significance but showed a strong trend when a Satterthwaite test was applied. In contrast, contingency table analysis, shown in FIG. 16, did achieve borderline significance. Overall, the results are considered to represent a strong trend.

TABLE 6

Contingency Table Analysis of Effects of Citrulline upon Duration of Respiratory Support

| Duration of Respiratory Support | Placebo | Citrulline |
|---|---|---|
| ≤50 hours | 3 | 7 |
| >50 hours | 8 | 2 |

Figure 17:
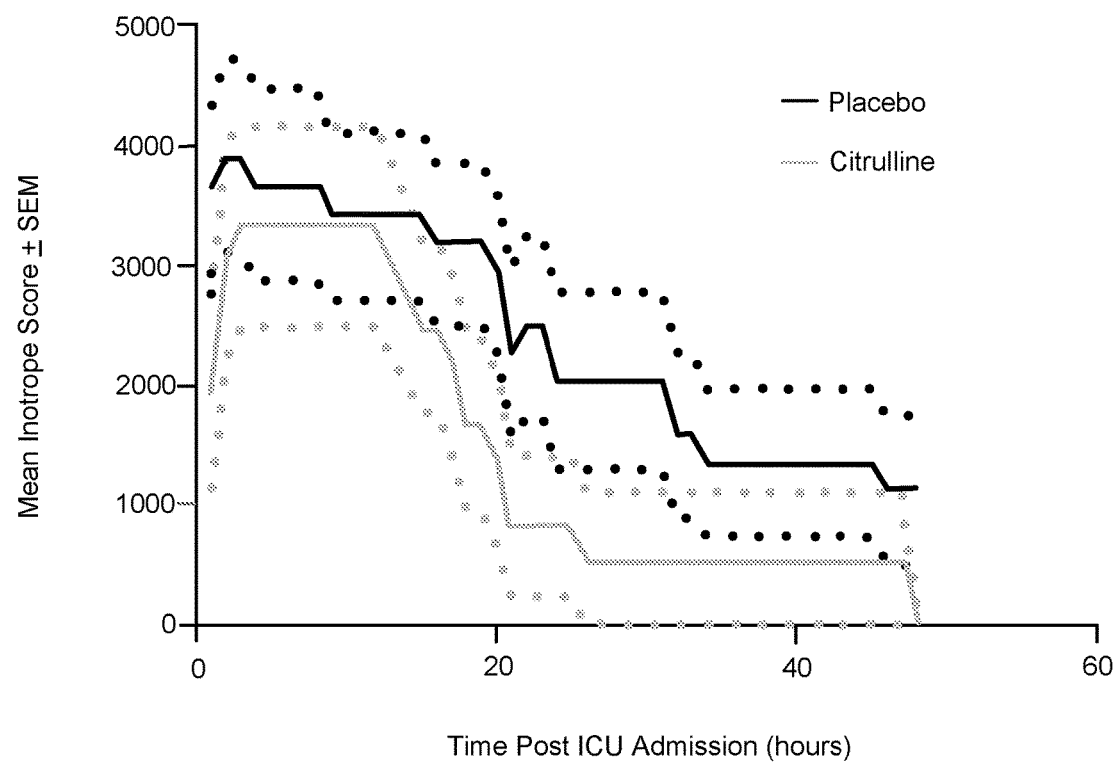
FIG. 17 depicts the mean Inotrope score of patients treated receiving citrulline (citrulline) versus those without citrulline (placebo).
Figure 18A:
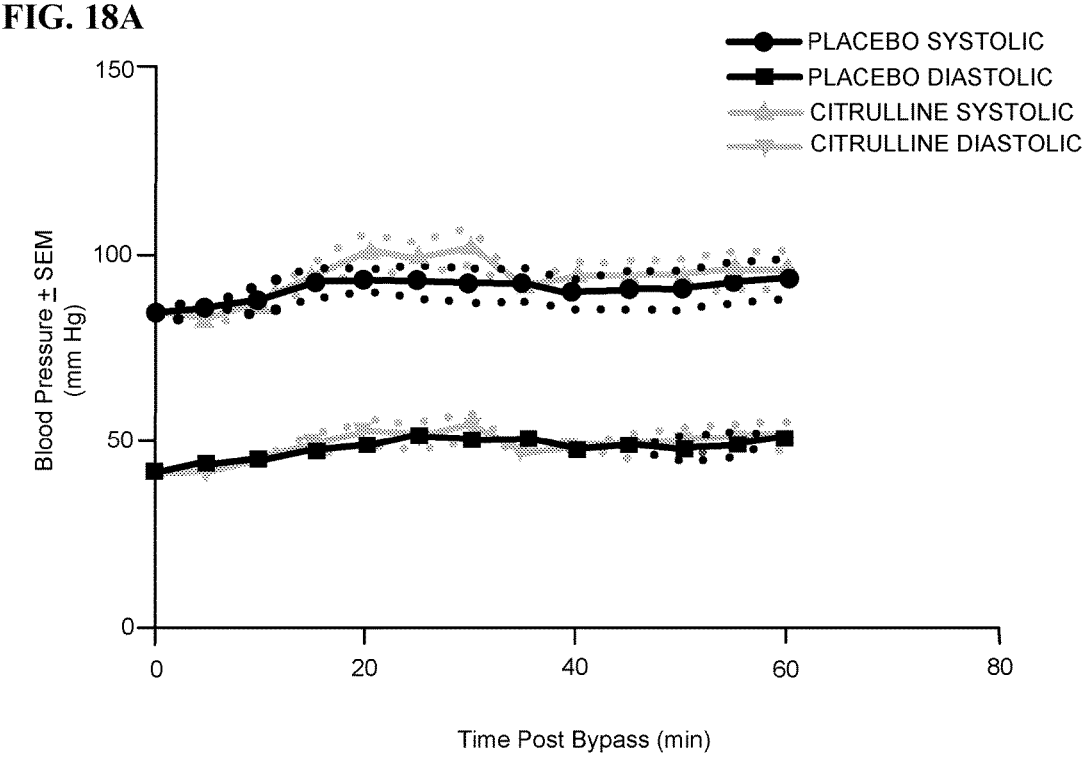
FIG. 18A-B depicts the systolic and diastolic blood pressure and mean arterial pressure of patients receiving citrulline (citrulline) versus those without citrulline (placebo).
Figure 18B:
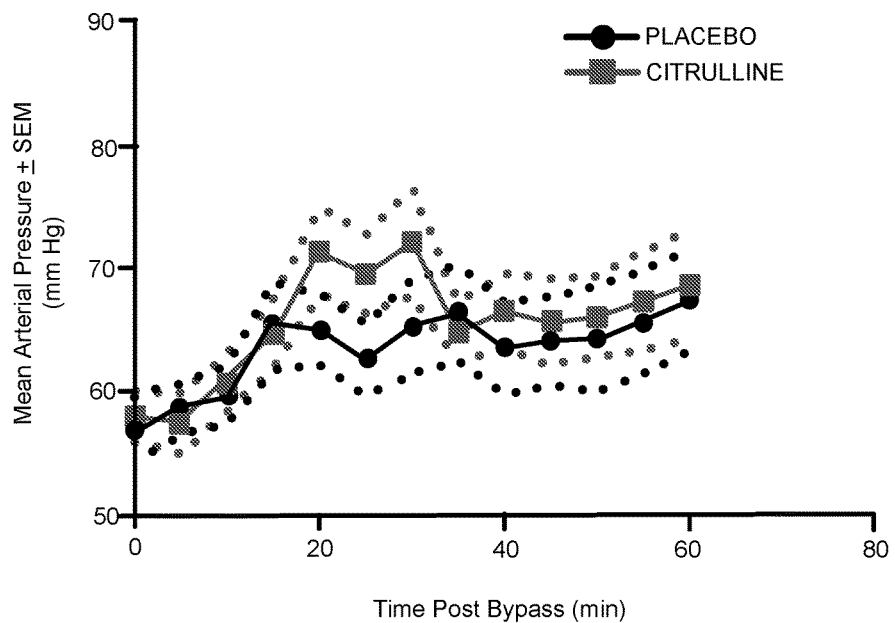

The cardiovascular parameters provide additional insights. FIG. 17 shows that the citrulline patients unexpectedly showed markedly better inotrope scores, particularly from 15 to 18 hours onward following ICU admission. Systolic blood pressure showed a mild transient elevation in the citrulline group commencing around 20 hours after cessation of bypass, while diastolic pressures were essentially identical between the two groups. FIG. 18A. Mean arterial pressure showed a slight transient increase in the citrulline group, as shown in FIG. 18B, reflective of the systolic pressure change. Given the transient nature of the systolic blood pressure elevation and arterial pressure elevation, the systolic pressure increase suggests a possible lesser need for inotropes than would be expected.

Duration of total respiratory support appears to be a viable endpoint for the study of citrulline to prevent acute pulmonary hypertension complicating congenital heart surgery repair. No adverse effects upon hemodynamic parameters were observed.

Example 9

Citrulline Formulation

Sterile citrulline may be produced first as a non-sterile bulk powder utilizing a process of bacterial (*Streptococcus faecalis*) fermentation of arginine followed by separation and extraction steps. The non-sterile bulk powder is then reconstituted and undergoes endotoxin reduction and sterile filtration steps followed by crystallization, drying, and micronization in an aseptic environment. The sterile bulk powder is then used as the "raw material" for aseptic filling into glass vials to produce the finished drug product which is reconstituted with a sterile diluent prior to use.

Each sterile vial of citrulline for injection may contain about 300 mg of sterile citrulline powder. Each vial may be reconstituted with 6 mL sterile water for injection, USP and is further diluted with about 5.9 mL of sodium chloride 0.9%, USP to equal a volume of 12 mL and a concentration of 300 mg/12 mL=25 mg/l mL. Exemplary patient infusions may be in sodium chloride 0.9%, USP to be administered at a concentration of about 25 mg/mL.

Example 10

Pharmacokinetics (PK) and Safety of IV L-Citrulline Administration to Children and Infants Undergoing Cardiopulmonary Bypass (CPB) for Surgical Repair of Congenital Heart Defects A multicenter, Phase IB single-blind, randomized, placebo controlled study was conducted to determine the pharmacokinetics (PK) and safety of IV L-citrulline administration to children and infants undergoing cardiopulmonary bypass (CPB) for surgical repair of congenital heart defects.

The primary objective of the study was to determine if a revised protocol of intravenous (IV) L-citrulline delivery given peri-operatively achieved a plasma citrulline level of >100 µmol/L in the group given citrulline and to compare that to citrulline levels in the placebo group, during follow-up in children undergoing surgical repair of an atrial septal defect (ASD) and/or a ventricular septal defect (VSD) or a partial or complete atrioventricular septal defect (AVSD).

Safety objectives were to further analyze the safety profile of citrulline and secondary objectives were to establish the impact of citrulline on postoperative clinical outcomes.

Twenty two (22) patients were enrolled and treated. The patients received study drug or placebo infusion according to a fixed dosing protocol starting at the initiation of CPB until 48 hours postoperatively or until removal of the arterial line. Study participation ended at discharge or at Day 28 whichever came first. The dosing regimen was designed to maintain plasma citrulline levels in the face of extended hemofiltration.

Twenty two (22) patients were enrolled and treated. Patients received an IV citrulline bolus of 150 mg/kg or placebo at the initiation of CPB, followed by the addition of L-citrulline at a concentration of 200 µmol/L or placebo to the filtration or hemoconcentration replacement fluid used during CPB. A citrulline bolus of 20 mg/kg was administered 30 minutes after decannulation from CPB, immediately followed by a 9-mg/kg/hr continuous infusion of citrulline or placebo for 48 hours. Study participation ended at discharge or at Day 28 whichever came first.

Plasma citrulline concentration levels were the primary PK variable; these were assessed in blood samples collected at 7 perioperative time points. Secondary PK variables were concentrations of arginine and nitric oxide (NO) metabolites in the same sample set. PK values were compared between groups.

Subjects received an IV citrulline bolus of 150 mg/kg or placebo at the initiation of CPB, followed by the addition of L-citrulline at a concentration of 200 µmol/L or placebo to the filtration or hemoconcentration replacement fluid used during CPB. A citrulline bolus of 20 mg/kg was administered 30 minutes after decannulation from CPB, immediately followed by a 9-mg/kg/hr continuous infusion of citrulline or placebo for 48 hours.

Primary safety assessments included hemodynamic monitoring to identify clinically significant hypotension using age-specific limits. Adverse event information was collected, and postoperative bleeding was recorded.

Further safety, laboratory, and clinical assessments were performed from baseline to discharge, secondary clinical variables included: postoperative mechanical ventilation, duration of total respiratory support, hemodynamic improvement, postoperative PVT by echocardiogram, serum creatinine and liver enzymes, inotrope score, duration of chest tube usage, length of intensive care unit stay, length of hospitalization and survival.

Analysis of the study results, is presently in its final stages but not all quality control has not been completed, meaning that the data that follows may be subject to minor change.

Figure 19:
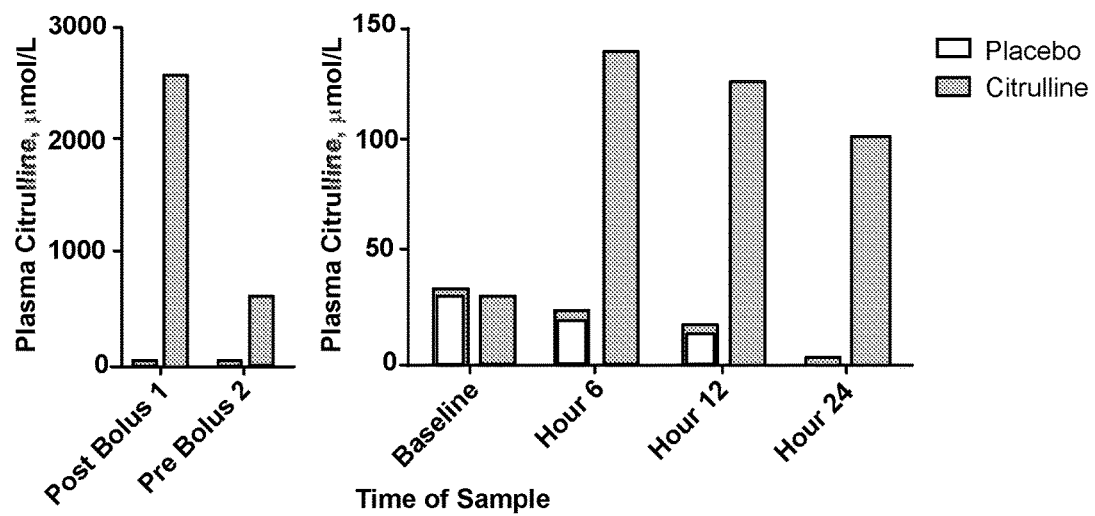
FIG. 19 depicts the median plasma citrulline levels in patients receiving pre-operative bolus, peri-operative, and post-operative citrulline.
Figure 20:
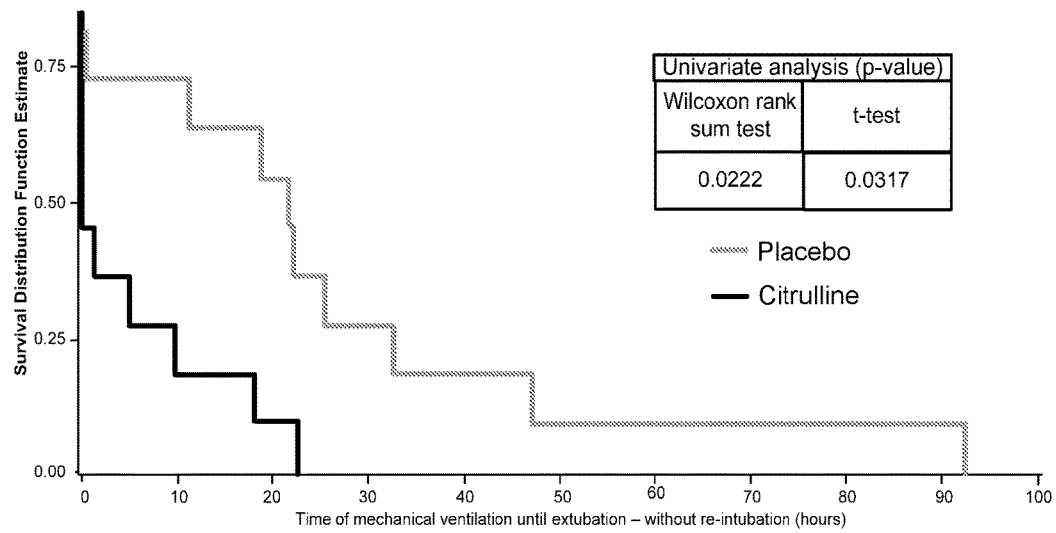
FIG. 20 Kaplan-Meier survival analysis of the duration of invasive mechanical ventilation from end of surgery until last extubation. (Excluding Re-intubation, censored). Patients receiving citrulline showed a reduced duration of mechanical ventilation. The differences in mechanical ventilation were statistically significant by the Wilcoxon rank sum test (p=0.0222) and by the ANOVA t-test (p=0.0317).

Notwithstanding, the analyses, detailed below, showed the following as either preferable to use a composite variable comprised of the longer of the durations of each of these parameters as a surrogate for the duration of stay in the intensive care unit. The reason for this preference is that the actual duration of ICU stay may be influenced by extraneous variables such as time of day and bed availability, among others. Patients receiving study drug showed shorter composite durations of mechanical ventilation and inotrope therapy than did patients receiving placebo. Thus, as assessed by the composite surrogate marker variable, patients receiving study drug were ready for discharge from the ICU sooner than patients receiving placebo. The revised dosing protocol achieved plasma citrulline levels consistently above the target level of 100 µmol/L as shown below in FIG. 19. Patients receiving citrulline showed a reduced duration of mechanical ventilation as shown in FIG. 20.

Some differences were noted in clinical practice among sites with regard to mechanical ventilation. One site tended to extubated patients in the operating room without recording a time of extubation for such patients. For purposes of analysis, the duration of postoperative mechanical ventilation was set to zero for such patients. When these patients were stratified by treatment, it was shown that all 6 patients (100%) receiving i.v. L-citrulline had been extubated in the operating room, in comparison to only 2 of 6 patients (33%) in the placebo group.

Figure 21:
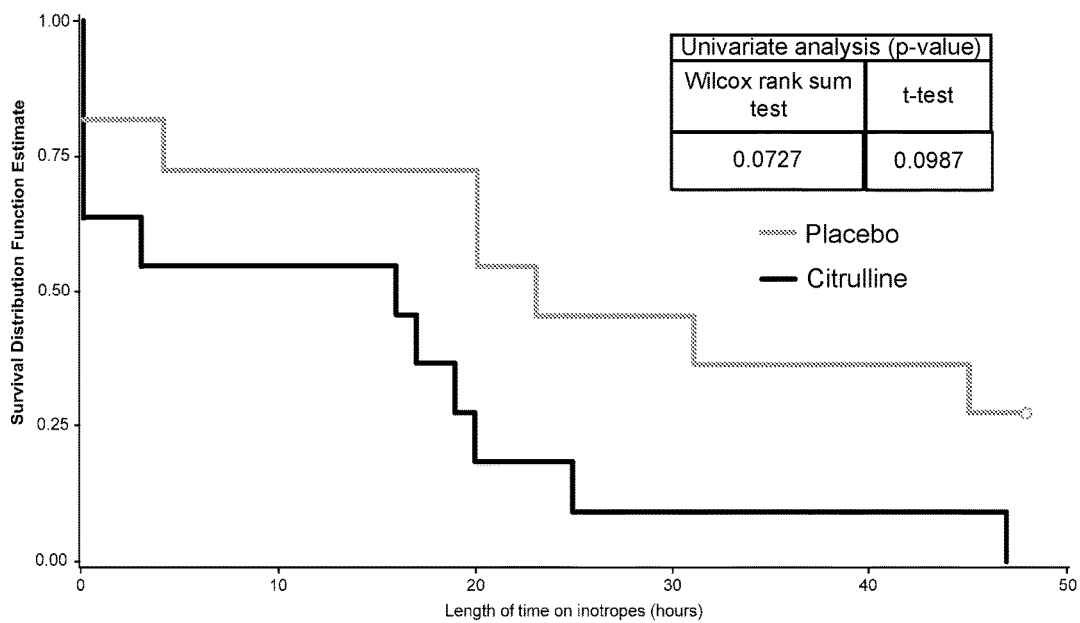
FIG. 21 depicts a Kaplan-Meier survival analysis of the length of time on inotropes. Univariate analysis (p-value): Wilcoxon rank sum test (0.0727); T-test (0.097).

As with the length of time of mechanical ventilation, the duration of inotrope therapy showed marked differences between the two treatment groups as shown in FIG. 21.

In FIG. 21, data are defined as the time between the start and end times of inotrope use. All missing or 0 total inotrope scores prior to the first measured score are set to 0 and are therefore not considered as being on inotropes. The total inotrope score is considered, which is calculated on the basis of Dopamine, Dobutamine, Milrinone, Epinephrine, Phenylephrine, and Norepinephrine. The length of time on inotropes of patients with no use of inotropes is set to 0 hours (not censored).

Figure 22:
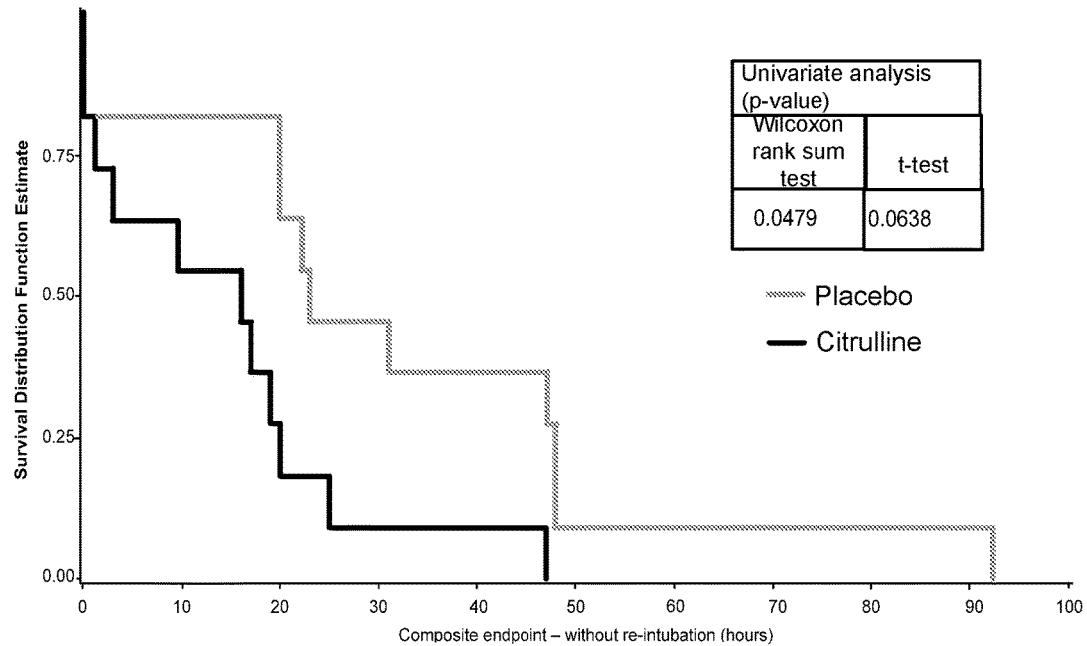
FIG. 22 depicts a Kaplan-Meier survival analysis of the length of time on inotropes. Univariate analysis (p-value): Wilcoxon rank sum test (0.0727); T-test (0.0987).

As previously mentioned, cessation of mechanical ventilation and of inotrope therapy are the two principal determinants of readiness for discharge from the intensive care unit. A composite variable comprising (for each subject) of the longer of the two parameters—duration of mechanical ventilation or of inotrope therapy—can serve as an effective and accurate surrogate for the duration of intensive care unit stay. FIG. 22 shows the differences in the composite variable when citrulline and placebo groups are compared. Patients receiving study drug showed shorter composite durations of mechanical ventilation and inotrope therapy than did patients receiving placebo. Thus, as assessed by the composite surrogate marker variable, patients receiving study drug were ready for discharge from the PICU sooner than patients receiving placebo. In addition to indicating shorter PICU time, shorter mechanical ventilation time lowers the added risk of physical injury.

In addition to achieving the targeted plasma citrulline levels, this study also yielded statistically significant and near significant results demonstrating citrulline treatment dependent differences in the duration of mechanical ventilation and inotrope therapy between the treated and control groups in a small group of 22 subjects.

The duration of postoperative invasive mechanical ventilation was derived as the time in hours from separation from cardiopulmonary bypass until endotracheal extubation. If a patient required reintubation within 24 hours after extubation, the reintubation time was added in the main analysis. In a second analysis, the reintubation time was not included.

Including the reintubation time, the mean duration of invasive mechanical ventilation was clearly longer in the placebo group than in the citrulline treatment group, with citrulline-treated patients needing only an average of 5 hours of invasive ventilation while placebo-treated patients needed 37 hours (Table 8). The difference did not reach statistical significance in the ANOVA test, most likely based on the large variation of durations in the placebo group. However, when the reintubation time was excluded, the difference between the group was still eminent and statistical significance was reached in the ANOVA ($p=0.0317$). Statistical significance for both analyses was shown by the Wilcoxon rank-sum test.

Cessation of positive pressure ventilation and inotrope therapy are the two principal determinants of readiness for discharge from the intensive care unit. Together, as a composite variable comprised of the longer of the duration of positive pressure ventilatory support or of inotrope therapy, they can serve as an effective surrogate for the duration of intensive care unit stay. This latter variable is subject to confounding factors that may adventitiously prolong it, such as lack of bed availability.

In summary, the data from this study shows that the administered dosing regimen achieved the pharmacokinetic endpoint. Further, despite the sample size of the study, this study demonstrated clear treatment-dependent differences in favor of citrulline for the duration of mechanical ventilation and inotrope therapy between the treated and control groups. Combined in a composite variable, the results show clinically meaningful therapeutic efficacy for citrulline for the time to discharge from the intensive care unit. Thus, the results of this study indicate that intravenous citrulline administration can play a beneficial role in preventing the clinical sequelae of cardiopulmonary bypass-induced pulmonary injury.

Example 10A

Pharmacokinetics Analysis

The citrulline concentration levels during and after the CPB procedure was the PK parameter of interest in this study. The target level in patients treated with intravenous citrulline was a plasma citrulline level of >100 µmol/L during the immediate follow-up period after CPB. Plasma blood collection was performed at 7 perioperative time points: at baseline before surgery, during CPB (post-bolus 1), and after surgery/CPB at the time points 0 hours (pre bolus 2), 6 hours, 12 hours, 24 hours, and 48 hours.

The mean and median citrulline concentrations at the respective time points are summarized by treatment group in Table 7. Across all sampling times with data available, the mean citrulline concentration in the citrulline treatment group exceeded the specified lower limit of 100 µmol/L, whereas the mean citrulline concentrations in the placebo group were below this threshold at all time points analyzed. Of note is the high mean baseline value in the citrulline group (200.9 µmol/L). One patient (02-004) in this group presented with a baseline citrulline level of 1919 µmol/L, i.e. prior to i.v. citrulline treatment. There is no information available as to why the baseline citrulline level was that high for this patient. Available data indicate that the baseline sample was drawn prior to the first treatment with citrulline. Baseline citrulline values in all other patients in this group were notably lower, ranging from 8 to 42 µmol/L.

TABLE 7

Citrulline concentrations [µmol/L] over time

| Time point of sample | Placebo (N = 11) | | | Citrulline (N = 11) | | |
|---|---|---|---|---|---|---|
| | n | Mean ± SD | Median | n | Mean ± SD | Median |
| Baseline | 11 | 34.1 ± 7.50 | 34.0 | 11 | 200.9 ± 569.89 | 32.0 |
| Post Bolus 1 | 11 | 29.5 ± 5.96 | 28.0 | 11 | 2405.9 ± 1517.4 | 2577.0 |
| Pre Bolus 2 | 11 | 30.6 ± 10.46 | 28.0 | 11 | 890.9 ± 1077.5 | 573.0 |
| Hour 6 | 11 | 24.1 ± 7.76 | 24.0 | 10 | 167.8 ± 117.67 | 138.0 |
| Hour 12 | 9 | 19.9 ± 7.01 | 18.0 | 10 | 127.1 ± 16.18 | 125.0 |
| Hour 24 | 9 | 12.9 ± 2.89 | 12.0 | 10 | 125.3 ± 38.74 | 114.0 |
| Hour 48 | 4 | 12.3 ± 3.40 | 11.5 | 0[a] | — | — |

[a]No 48 hour sampling data are available for citrulline patients. One patient (01-007) had a sample collected at 46 h, but was not included in 48 h analysis since the sample was considered an unscheduled assessment. Another patient (02-010) received continuous infusion for 47.5 h, but no data are available for the 48 h time point.
SD = standard deviation,
N = number of patients,
n = number of patients with data available.

Median citrulline values are therefore more appropriate to depict the changes in citrulline concentrations over time. The median citrulline values during the CPB procedure and at baseline in comparison to post-surgery are shown graphically in FIG. 19. A notable increase in median citrulline levels in the citrulline treatment group compared to the placebo group can be seen at all post-CPB follow-up time points.

Only 5 of the total of 59 samples taken in the citrulline treatment group (excluding baseline samples) showed plasma citrulline levels <100 μmol/L (Table 8). In comparison, all samples taken from placebo-treated patients had citrulline levels <100 μmol/L. This difference in citrulline concentrations was highly statistically significant (p=0.0006).

TABLE 8

Samples with citrulline concentrations ≥100 μmol/L

|  | Number of samples with | Placebo (N = 11) | Citrulline (N = 11) |
|---|---|---|---|
| Site 01 | Citrulline ≤100 μmol/L | 27 | 2 |
|  | Citrulline >100 μmol/L | 0 | 25 |
| Site 02 | Citrulline ≤100 μmol/L | 32 | 3 |
|  | Citrulline >100 μmol/L | 0 | 29 |
| CMH p-value |  | 0.0006 |  |

Note:
All samples except for the baseline sample were used for analysis. Cochrane-Mantel-Haenszel test based on whether a patient had any citrulline levels above 100 μmol/L.

Citrulline is the precursor of arginine and nitric oxide. A summary of arginine and nitric oxide values at each of the sampling time points is provided in Table 9.

TABLE 9

Arginine and nitric oxide concentrations over time

| Time point of sample | Placebo (N = 11) | | | Citrulline (N = 11) | | |
|---|---|---|---|---|---|---|
|  | n | Mean ± SD | Median | n | Mean ± SD | Median |
| Arginine [μmol/L] | | | | | | |
| Baseline | 11 | 58.7 ± 12.37 | 55.0 | 11 | 49.6 ± 15.72 | 50.0 |
| Post Bolus 1 | 11 | 47.7 ± 7.43 | 46.0 | 11 | 72.6 ± 30.02 | 60.0 |
| Pre Bolus 2 | 11 | 67.1 ± 11.66 | 66.0 | 11 | 145.1 ± 47.94 | 141.0 |
| Hour 6 | 11 | 47.3 ± 12.29 | 47.0 | 10 | 67.0 ± 22.66 | 66.5 |
| Hour 12 | 9 | 39.0 ± 12.04 | 35.0 | 10 | 61.5 ± 17.37 | 57.5 |
| Hour 24 | 9 | 28.1 ± 12.56 | 30.0 | 10 | 65.8 ± 18.80 | 64.0 |
| Hour 48 | 4 | 34.5 ± 15.33 | 29.5 | 0 | — | — |
| Nitric Oxide [μmol/L] | | | | | | |
| Baseline | 11 | 69.5 ± 41.34 | 56.7 | 11 | 31.6 ± 13.51 | 36.6 |
| Post Bolus 1 | 11 | 51.3 ± 38.83 | 44.1 | 11 | 25.3 ± 12.76 | 25.0 |
| Pre Bolus 2 | 11 | 48.8 ± 29.16 | 38.4 | 11 | 30.7 ± 12.64 | 31.0 |
| Hour 6 | 11 | 59.9 ± 45.59 | 37.5 | 10 | 32.0 ± 16.97 | 26.0 |
| Hour 12 | 9 | 62.0 ± 42.89 | 51.5 | 10 | 26.6 ± 13.43 | 23.6 |
| Hour 24 | 9 | 51.1 ± 42.58 | 46.8 | 10 | 29.1 ± 12.14 | 32.2 |
| Hour 48 | 4 | 42.5 ± 17.48 | 48.9 | 0 | — | — |

SD = standard deviation,
N = number of patients,
n = number of patients with data available.

Figure 24A:
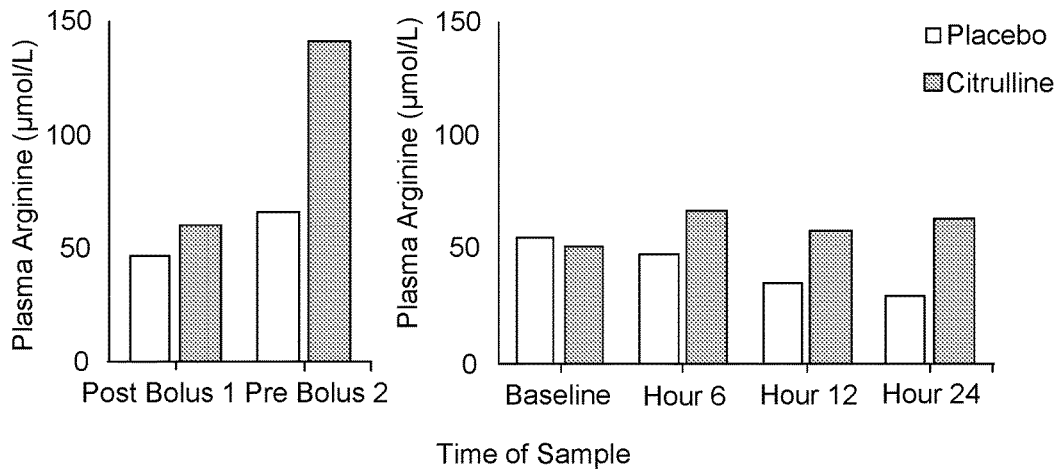
FIG. 24A-B depicts median plasma arginine levels (FIG. 24A) and median plasma nitric oxide (NO) levels (FIG. 24B) in patients receiving a placebo and citrulline
Figure 24B:
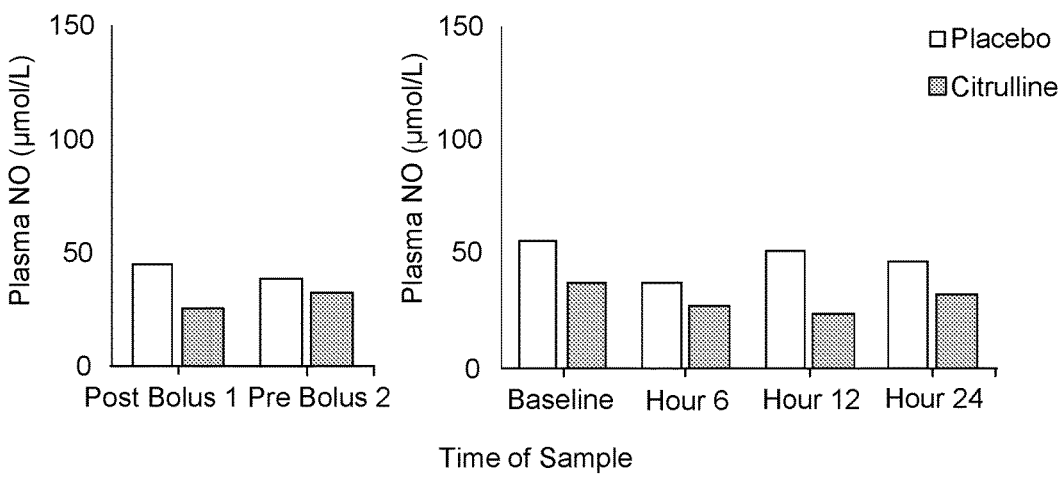

Median values are also shown graphically in FIG. 24A and FIG. 24B. Unlike citrulline, plasma arginine in citrulline-treated patients was only slightly elevated immediately following the first citrulline bolus. This lag in the rise in arginine levels likely reflects the time needed for citrulline to become available for the synthesis of arginine. Consequently, a notable rise of arginine in citrulline-treated patients in comparison to placebo-treated patients is shown at the pre-bolus 2 time point. Post-surgery, arginine levels in the citrulline group remained elevated at around 60 μmol/L, while they dropped to about 30 μmol/L in the placebo group.

Plasma nitric oxide levels remained more or less unchanged across the sampling time points in each of the treatment groups. This result may not be surprising since the production of nitric oxide is a local phenomenon. The addition of citrulline is expected to improve the local, tightly-regulated NO production; however, the increase would probably not show up on a molar basis in the bloodstream.

Example 10B

Postoperative Invasive Mechanical Ventilation

The duration of postoperative invasive mechanical ventilation was derived as the time in hours from separation from cardiopulmonary bypass until endotracheal extubation. If a patient required reintubation within 24 hours after extubation, the reintubation time was added in the main analysis. In a second analysis, the reintubation time was not included.

Only one patient in the placebo group required re-intubation. The patient (02-011) was first extubated on Day 4 after the end of CPB, but was re-intubated the following day and remained intubated for another 6 days.

Including the reintubation time, the mean duration of invasive mechanical ventilation was clearly longer in the placebo group than in the citrulline treatment group, with citrulline-treated patients needing only an average of 5 hours of invasive ventilation while placebo-treated patients needed 37 hours (Table 10). The difference did not reach statistical significance in the ANOVA test, most likely based on the large variation of durations in the placebo group. However, when the reintubation time was excluded, the difference between the group was still eminent and statistical significance was reached in the ANOVA (p=0.0317). Statistical significance for both analyses was shown by the Wilcoxon rank-sum test.

TABLE 10

Duration of invasive mechanical ventilation [hours]

|  | Placebo (N = 11) | Citrulline (N = 11) | Diff (CI) t-test p-value Wilcoxon rank-sum test p-value |
|---|---|---|---|
| Re-intubation time included | | | |
| Mean ± SD | 37.1 ± 65.41 | 5.1 ± 8.15 | 32.0 (−9.5, 73.4) 0.1233 |
| Median | 21.7 | 0.0 | 0.0222 |
| Range | 0.0-229.3 | 0.0-22.5 |  |
| Re-intubation time excluded | | | |
| Mean ± SD | 24.7 ± 26.83 | 5.1 ± 8.15 | 19.5 (1.9, 37.2) 0.0317 |
| Median | 21.7 | 0.0 | 0.0222 |
| Range | 0.0-92.3 | 0.0-22.5 |  |

Figure 25A:
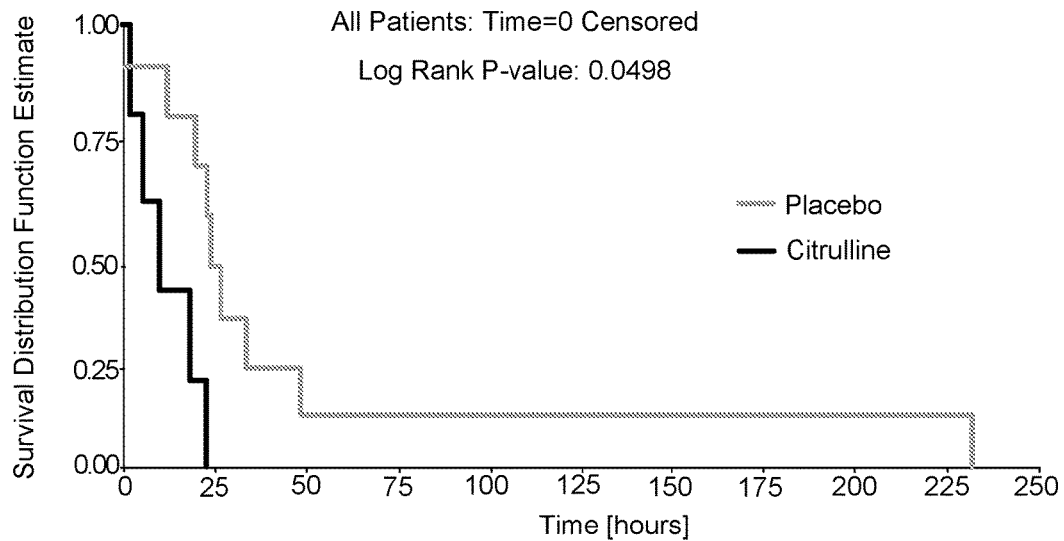
FIG. 25A-B depicts the duration of invasive mechanical ventilation in patients receiving a placebo and citrulline with re-intubation time included.
Figure 25B:
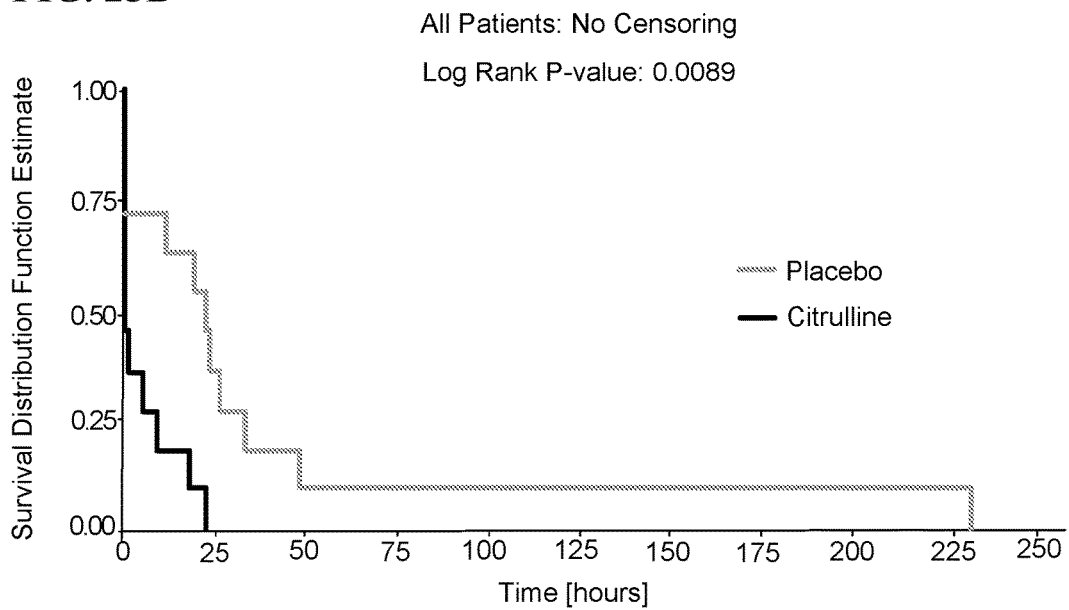

Kaplan-Meier survival analyses confirmed the reduced duration of invasive mechanical ventilation in the citrulline group, compared to the placebo group. FIG. 25A-B shows the duration of mechanical ventilation for the two treatment groups with reintubation times included. Site 02 tended to extubate patients in the operating room (OR) and generally did not record a time of extubation for these patients. Interestingly, out of 8 patients with an OR extubation at Site 02, 6 had received citrulline treatment and only 2 had received placebo. In the first analysis, the duration of postoperative mechanical ventilation for these patients was set to zero and all patients with ventilation time zero were censored (FIG. 25A). In a second analysis, patients with zero ventilation time were not censored (FIG. 25B). Both analyses showed statistically significant differences between the treatment groups based on the log rank test (p=0.0498 and p=0.0089, respectively).

Figure 26A:
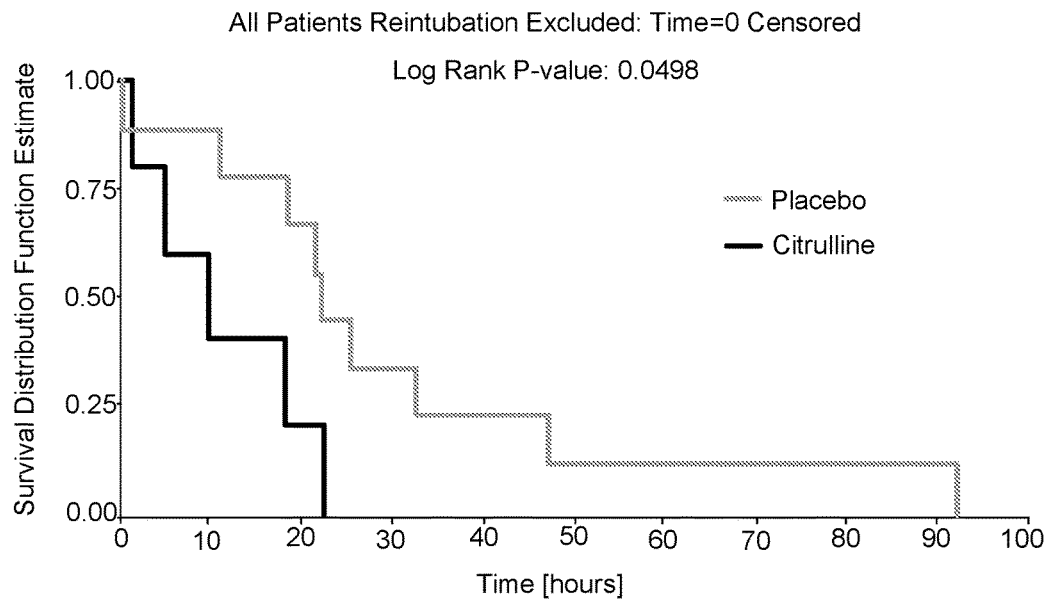
FIG. 26A-B depicts the duration of invasive mechanical ventilation (re-intubation time excluded) in one patient. The results confirm a beneficial effect of citrulline as compared to placebo treatment in a statistically significant decrease in the time with invasive mechanical ventilation.
Figure 26B:
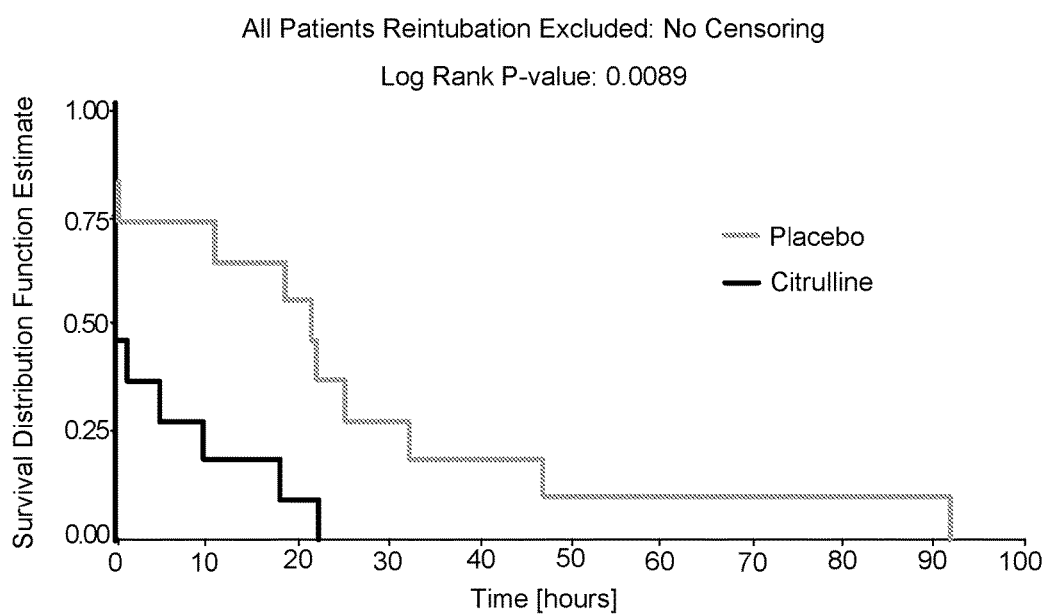

Kaplan Meier curves for the duration of invasive mechanical ventilation excluding the re-intubation time in the one patient are shown in FIG. 26A-B. The results confirmed the advantage of citrulline over placebo treatment and showed statistical significance in favor of citrulline in both analyses.

Example 10C

Total Respiratory Support

The analysis of total respiratory support includes any invasive and non-invasive respiratory support required during the study period. The mean total duration of respiratory support in the citrulline treatment group was less than half the duration in the placebo treatment group; the difference was statistically significant (Table 11).

TABLE 11

Total duration of respiratory support [hours]

|  | Placebo (N = 11) | Citrulline (N = 11) | Diff (CI) t-test p-value Wilcoxon rank-sum test p-value |
|---|---|---|---|
| n | 11 | 11 | 50.7 (5.4, 96.0) |
| Mean ± SD | 81.9 ± 66.23 | 31.2 ± 28.27 | 0.0301 |
| Median | 73.1 | 23.6 | 0.0418 |
| Range | 4.0-229.3 | 0.0-100.1 |  | n = patients with data available.

Figure 27A:
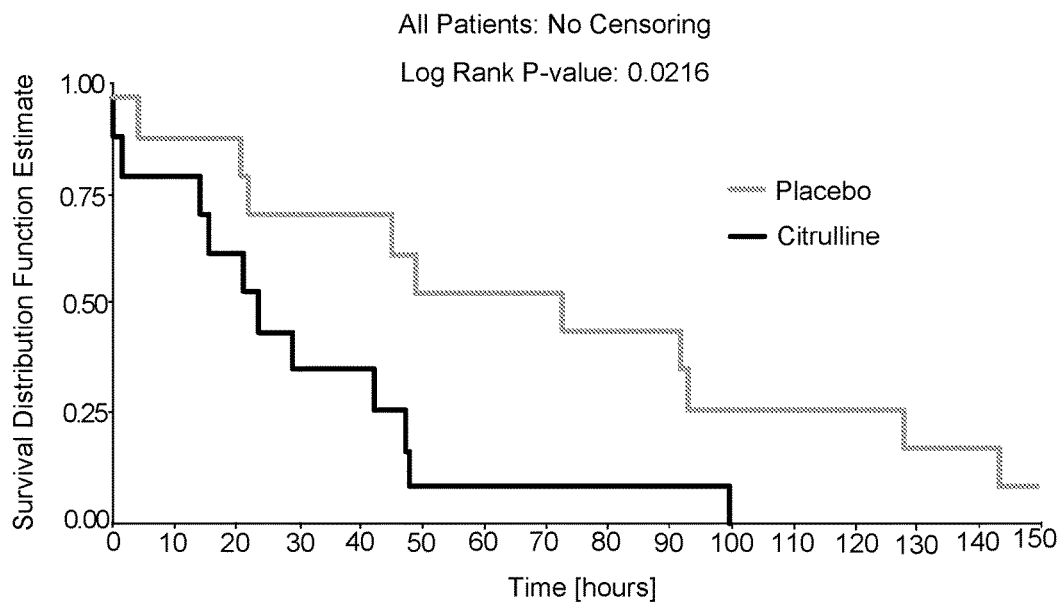
FIG. 27A-B depicts Kaplan-Meier survival plots showing a decrease in the need for respiratory support in patients receiving citrulline as compared to a placebo.
Figure 27B:
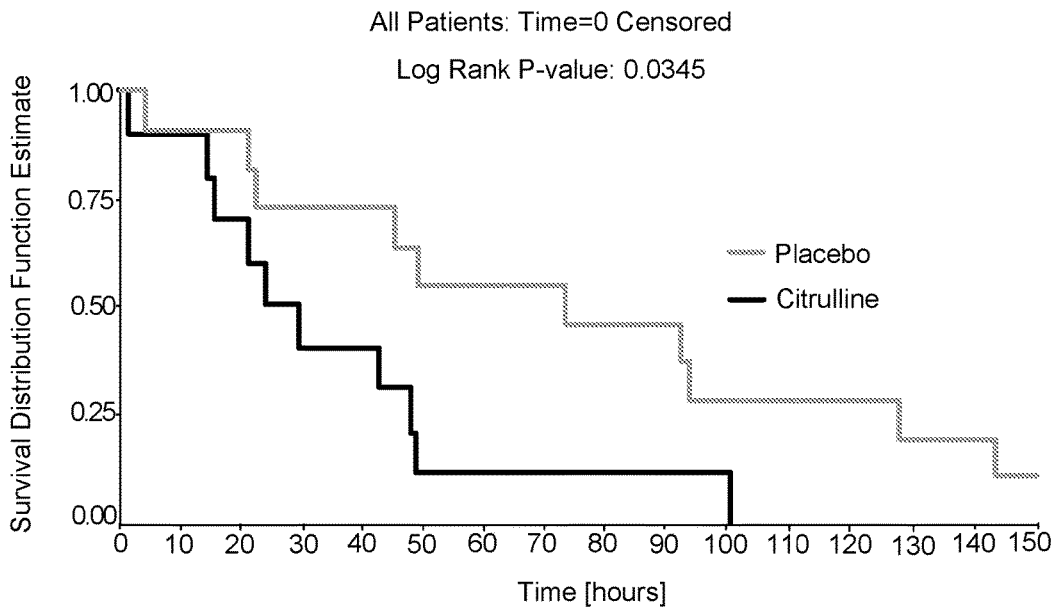

Kaplan-Meier survival plots confirming the advantage of citrulline over placebo treatment are shown for all patients (no censoring) and for patients without respiratory support censored in FIG. 27A-B.

Example 10D

Length of Time on Inotropes and Inotrope Score

The length of time on IV inotropes was documented from the time of first use after surgery until completion of the study medication at 48 hours, i.e. the duration of inotrope use was maximally 48 hours in the current analysis. Patients still receiving inotropes at hour 48 after surgery were censored. The average duration of intravenous (IV) inotrope use was clearly lower in the citrulline group than in the placebo group (Table 12). However, statistical significance for the between-treatment difference was not reached.

TABLE 12

Intravenous inotrope duration [hours]

|  | Placebo (N = 11) | Citrulline (N = 11) | Diff (CI) t-test p-value Wilcoxon rank-sum test p-value |
|---|---|---|---|
| Length of time on i.v. inotropes |  |  |  |
| Mean ± SD | 26.1 ± 19.38 | 13.4 ± 14.78 | 12.7 (−2.6, 28.1) 0.0987 |

TABLE 12-continued

Intravenous inotrope duration [hours]

|  | Placebo (N = 11) | Citrulline (N = 11) | Diff (CI) t-test p-value Wilcoxon rank-sum test p-value |
|---|---|---|---|
| Median | 23.0 | 16.0 | 0.0727 |
| Range | 0.0-48.0 | 0.0-47.0 |  |

Figure 28A:
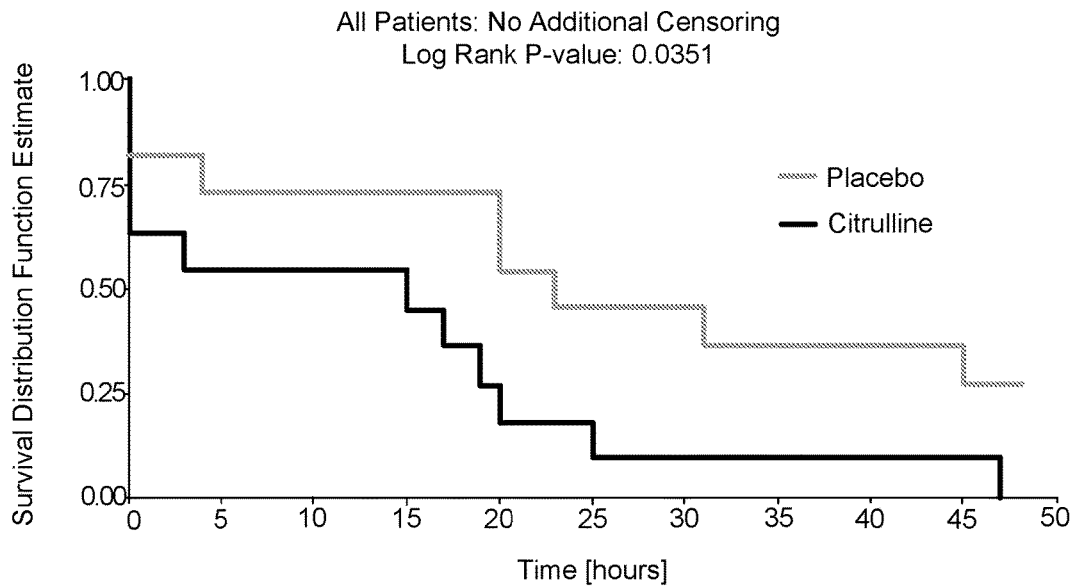
FIG. 28A-B depicts a Kaplan-Meier analysis (omitting patients with zero duration of intravenous (i.v.) inotrope use).
Figure 28B:
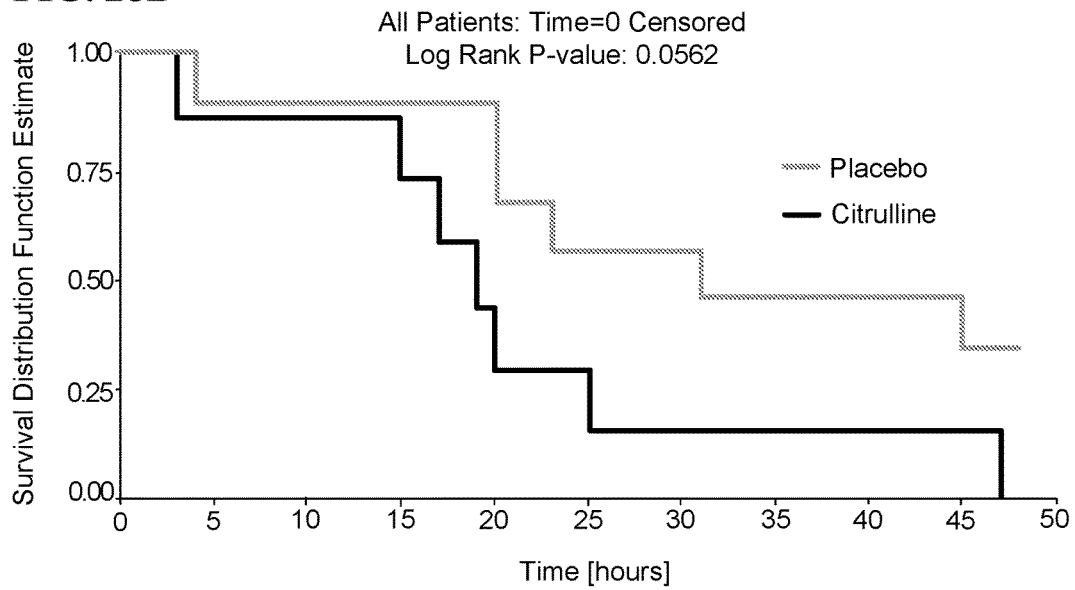

Survival analysis plots for the length of time on intravenous (IV) inotropes are presented in FIG. 28A-B. The primary Kaplan-Meier analysis censored patients still using inotropes at hour 48, but applied no additional censoring (FIG. 27A). A second analysis also censored patients without inotrope use, i.e. inotrope time=0 (FIG. 27B). Both analyses showed marked differences in the duration of inotrope use between the citrulline and the placebo groups. The advantage of citrulline treatment over placebo treatment was statistically significant in the main analysis without any additional censoring (p=0.0351, log-rank test).

Figure 29:
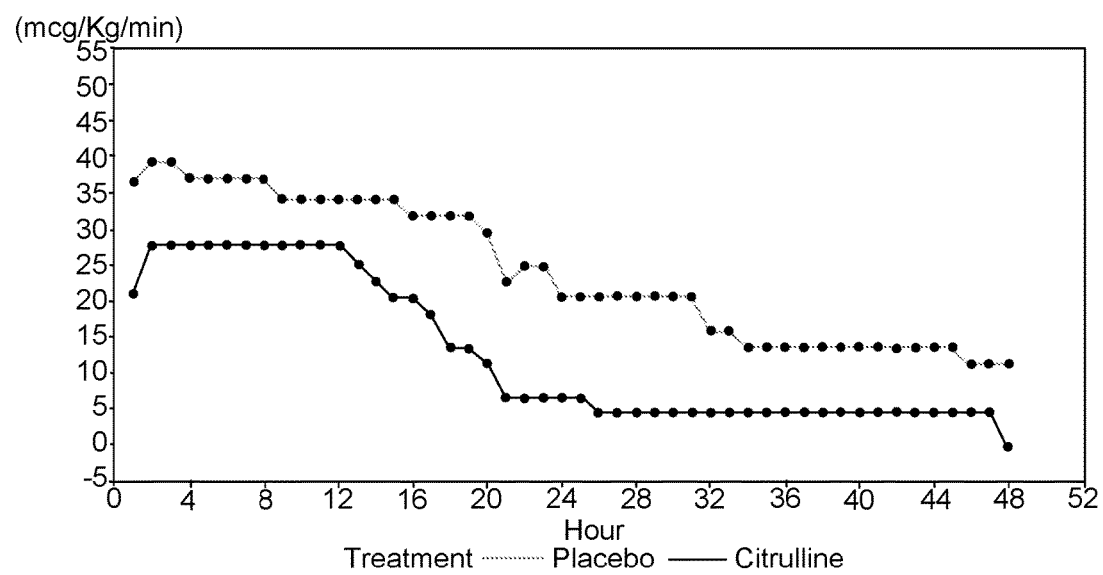
FIG. 29 depicts the mean inotrope scores over time, comparing patients receiving a placebo versus citrulline.

A third Kaplan-Meier analysis was performed omitting patients with zero duration of i.v. inotrope use. The results were identical to those for the overall population with time=0 censored. The total inotrope score, summarizing the use of all intravenous (IV) inotropes postoperatively, was notably lower in the citrulline group compared to the placebo group (Table 13). The difference in inotrope score was evident over the entire post-operation time analyzed (FIG. 29). The advantage for citrulline in inotrope use based on the total inotrope score was statistically significant in a repeated measures ANOVA (p=0.0438).

TABLE 13

Inotrope score

|  | Placebo (N = 11) | Citrulline (N = 11) | Diff (CI) t-test p-value Wilcoxon rank-sum test p-value |
|---|---|---|---|
| Total inotrope score |  |  |  |
| Mean ± SD | 1162.6 ± 951.31 | 602.7 ± 727.86 | 559.8 (−193.5, 1313.2) 0.1368 |
| Median | 1000.0 | 650.0 | 0.1271 |
| Range | 0.0-2617.1 | 0.0-2351.0 |  |

Example 10E

Vasoactive Medications

Figure 30A:
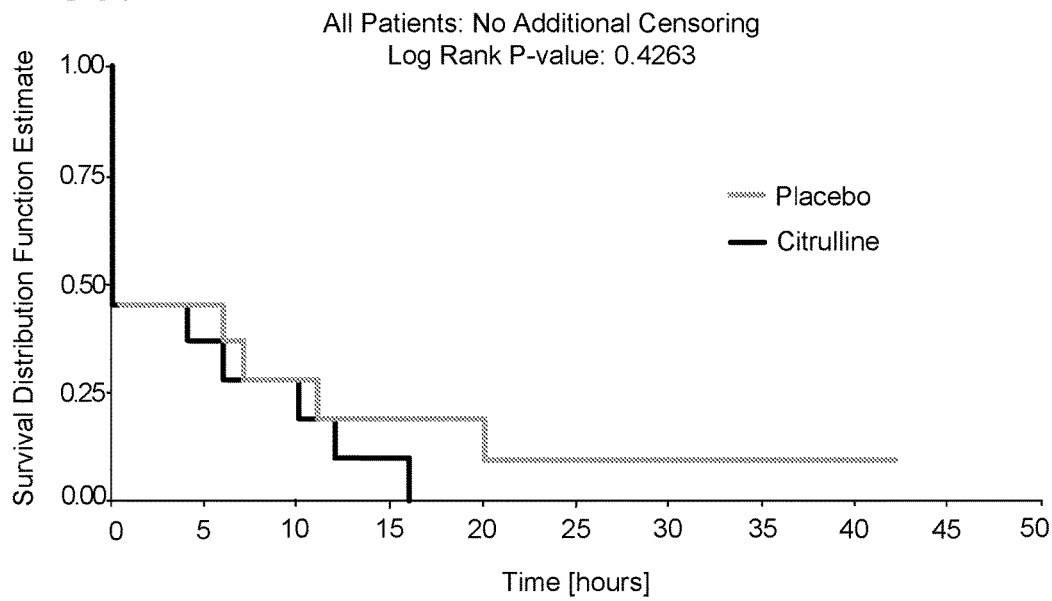
FIG. 30A-B depicts Kaplan-Meier plots for the total duration of vasoactive medications for all patients censoring (FIG. 30A) and for patients without vasoactive medication use censored (FIG. 30B).
Figure 30B:
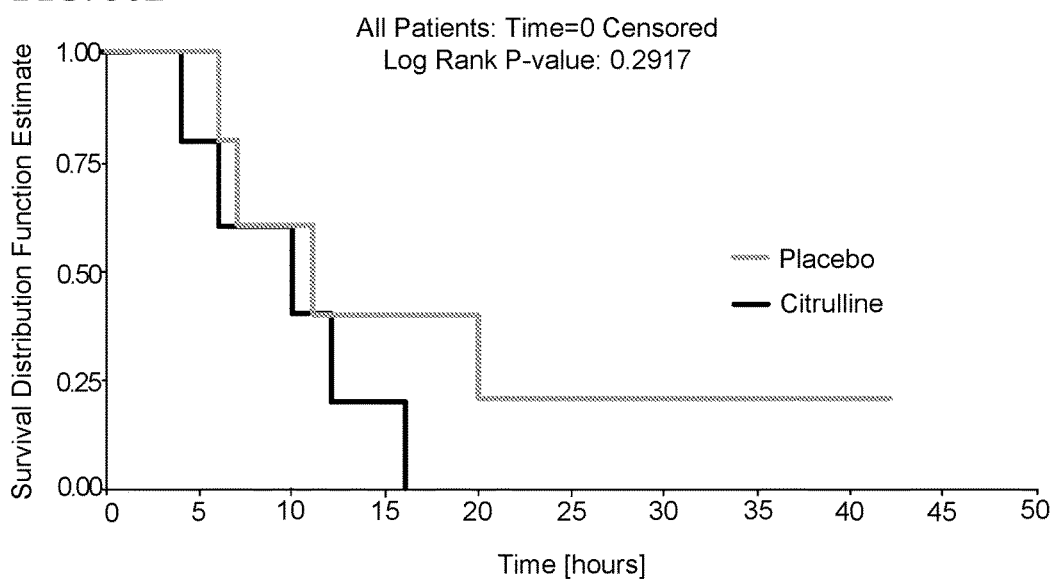

The total number of hours on vasoactive medications, including nitroglycerin, nitroprusside and vasopressin, was calculated from the end of surgery until the discontinuation of vasoactive medications or end of study medication (Hour 48), whichever occurred first. Table 14 compares the length of time on vasoactive medications for the citrulline and placebo treatment groups. The overall duration of concomitant vasoactive treatment was shorter in citrulline—than placebo-treated patients, but the difference was not statistically significant. Similar results are shown for the total vasoactive score. However, the patient receiving citrulline did, in fact, show a shorter total duration of vasoactive medication as shown in FIG. 30.

TABLE 14

Use of vasoactive medications

|  | Placebo (N = 11) | Citrulline (N = 11) | Diff (CI) t-test p-value Wilcoxon rank-sum test p-value |
|---|---|---|---|
| Length of time on vasoactive medications [hours] | | | |
| Mean ± SD | 9.8 ± 15.09 | 6.3 ± 7.18 | 3.5 (−7.0, 14.1) 0.4898 |
| Median | 0.0 | 1.0 | 0.9720 |
| Range | 0.0-48.0 | 0.0-17.0 | |
| Total vasoactive score | | | |
| Mean ± SD | 10.6 ± 17.42 | 5.5 ± 10.62 | 5.2 (−7.7, 18.0) 0.4125 |
| Median | 0.0 | 1.1 | 0.8884 |
| Range | 0.0-56.0 | 0.0-35.5 | |

Example 10F

Duration of ICU Stay

Duration of ICU stay was analyzed once as the total number of postoperative hours spent in the ICU and once as the total number of postoperative hours that a patient required postoperative mechanical ventilator or continuous intravenous inotrope or vasodilator support. The latter combination of parameters represents another surrogate endpoint for ICU stay.

Using either definition, the duration of ICU stay was clearly longer for patients treated with placebo than for patients treated with citrulline (Table 15). Excluding the time of re-intubation for one patient in the placebo group, the duration of ICU stay in citrulline-treated patients was still only about half as long as the duration for placebo-treated patients. Statistical significance for the between-treatment difference was shown in the Wilcoxon test.

TABLE 15

Duration of ICU stay

|  | Placebo (N = 11) | Citrulline (N = 11) | Diff (CI) t-test p-value Wilcoxon rank-sum test p-value |
|---|---|---|---|
| Duration of PICU stay [hours] | | | |
| Mean ± SD | 105.08 ± 187.762 | 35.94 ± 16.150 | 69.14 (−49.39, 187.67) 0.2379 |
| Median | 48.77 | 28.52 | 0.1891 |
| Range | 20.1-666.2 | 20.8-72.0 | |
| Longest duration of mechanical ventilation, i.v. inotrope use, or vasodilator use - re-intubation included [hours] | | | |
| Mean ± SD | 44.4 ± 63.62 | 14.5 ± 13.99 | 29.9 (−11.0, 70.9) 0.1430 |
| Median | 23.0 | 15.0 | 0.0479 |
| Range | 0.0-229.3 | 0.0-47.0 | |
| Longest duration of mechanical ventilation, i.v. inotrope use, or vasodilator use - re-intubation excluded [hours] | | | |
| Mean ± SD | 32.0 ± 26.26 | 14.5 ± 13.99 | 17.5 (−1.2, 36.2) 0.0653 |
| Median | 23.0 | 15.0 | 0.0479 |
| Range | 0.0-92.3 | 0.0-47.0 | |

Figure 31:
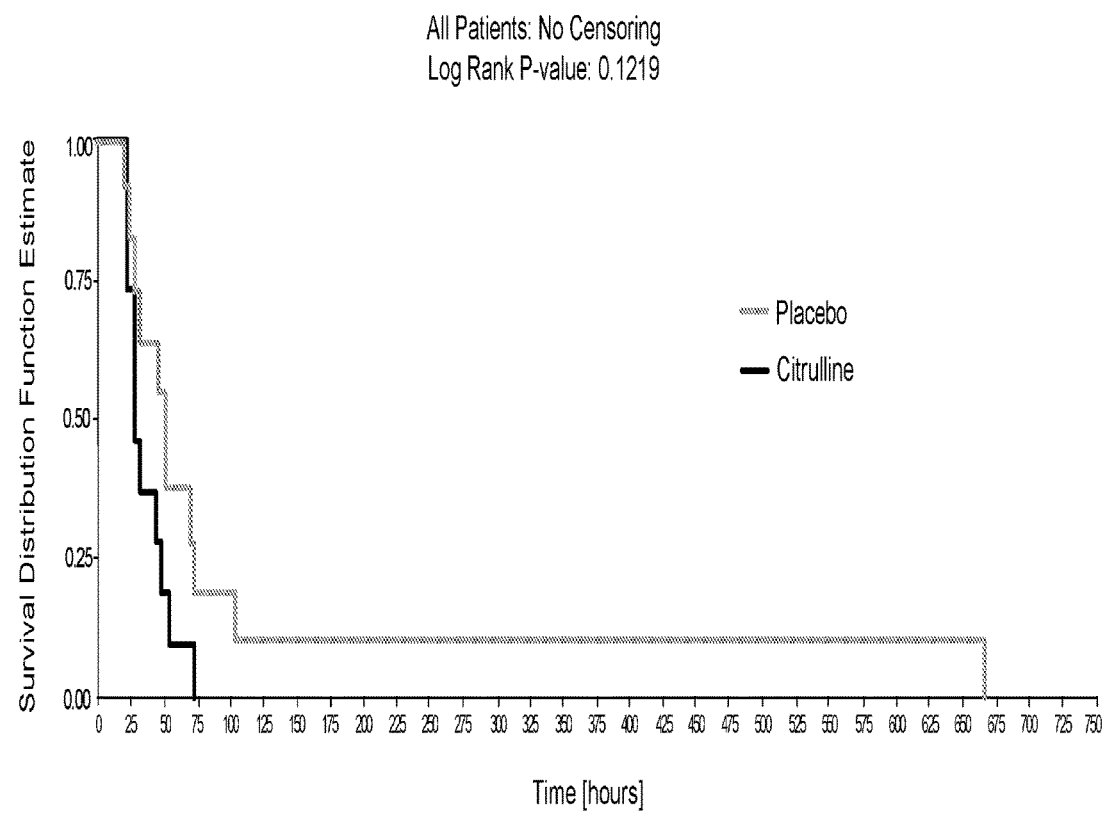
FIG. 31 depicts that total duration of Pediatric Intensive Care Unit (PICU) stay for patients receiving citrulline versus placebo.
Figure 32A:
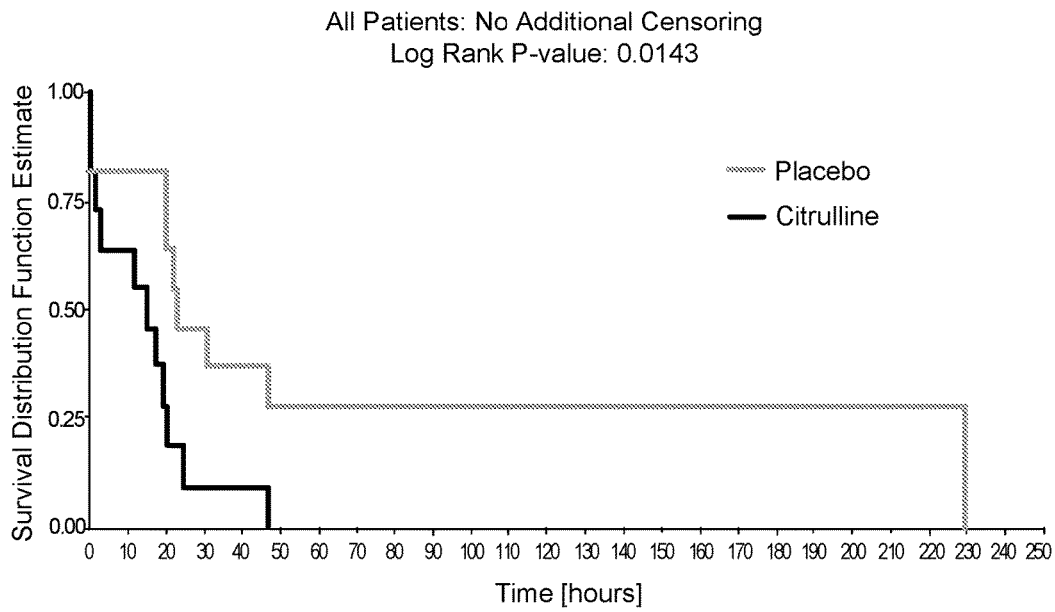
FIG. 32A-B depicts the total duration of Intensive Care Unit (ICU) stay based on longest duration of mechanical ventilation, i.v. inotrope use, or vasodilator use.
Figure 32B:
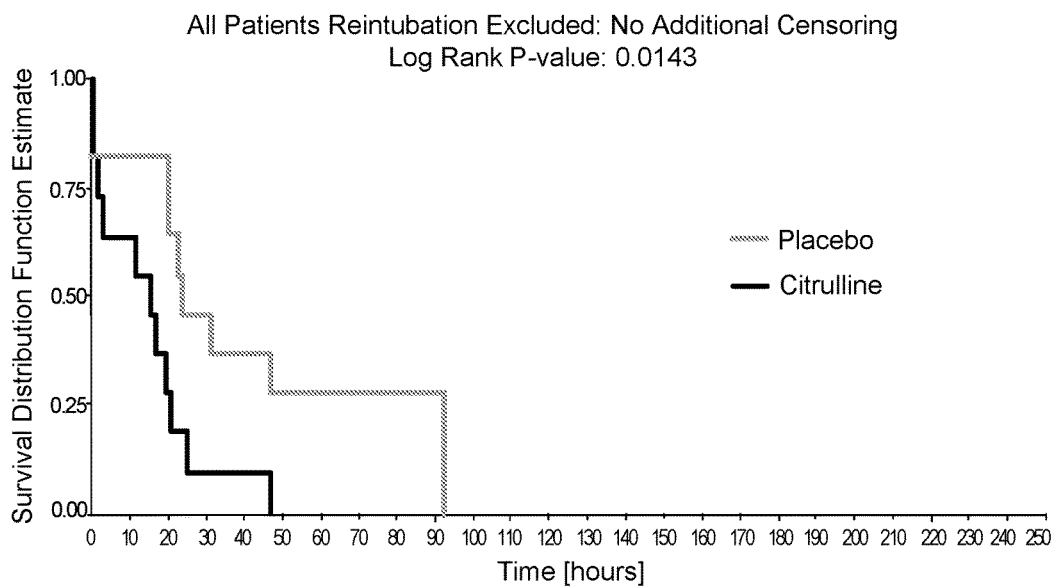

Kaplan-Meier plots of the total duration of PICU stay as well as the duration of ICU stay according to the definition of longest duration are shown in FIG. 31 and FIG. 32A-B. Particularly the survival analyses of the longest duration definition of ICU stay confirmed the advantage of citrulline over placebo, with statistical significance shown in both analyses.

Example 10G

Composite Endpoint

The cessation of positive pressure ventilation and of inotrope therapy are the two principal determinants of readiness for discharge from the intensive care unit. They were combined as a composite variable to serve as an additional effective surrogate endpoint for the duration of ICU stay.

The composite endpoint comprised the longer of the duration of positive pressure ventilatory support or of inotrope therapy. Since inotrope use was only documented until Hour 48 after surgery (end of study medication treatment), patients with inotrope use continuing until Hour 48 and with mechanical ventilation duration of ≤48 h were censored at this time point. If mechanical ventilation was continued beyond the 48-hour time point, the duration of mechanical ventilation was used in the analysis.

Table 16 summarizes the results for the composite endpoint including and excluding the re-intubation time for the one patient in the placebo group requiring re-intubation for additional mechanical ventilation. Also, for the combination of invasive mechanical ventilation and inotrope requirement, there was a clear advantage for citrulline compared to placebo treatment. The between-treatment differences were statistically significant in the Wilcoxon rank-sum test.

TABLE 16

Composite analysis of duration of invasive mechanical ventilation or inotrope use [hours]

|  | Placebo (N = 11) | Citrulline (N = 11) | Diff (CI) t-test p-value Wilcoxon rank-sum test p-value |
|---|---|---|---|
| Re-intubation time included | | | |
| Mean ± SD | 44.4 ± 63.62 | 14.3 ± 14.06 | 30.2 (−10.8, 71.1) 0.1403 |
| Median | 23.0 | 15.0 | 0.0479 |
| Range | 0.0-229.3 | 0.0-47.0 | |
| Re-intubation time excluded | | | |
| Mean ± SD | 32.0 ± 26.26 | 14.3 ± 14.06 | 17.7 (−1.0, 36.4) 0.0625 |
| Median | 23.0 | 15.0 | 0.0479 |
| Range | 0.0-92.3 | 0.0-47.0 | |

Figure 33A:
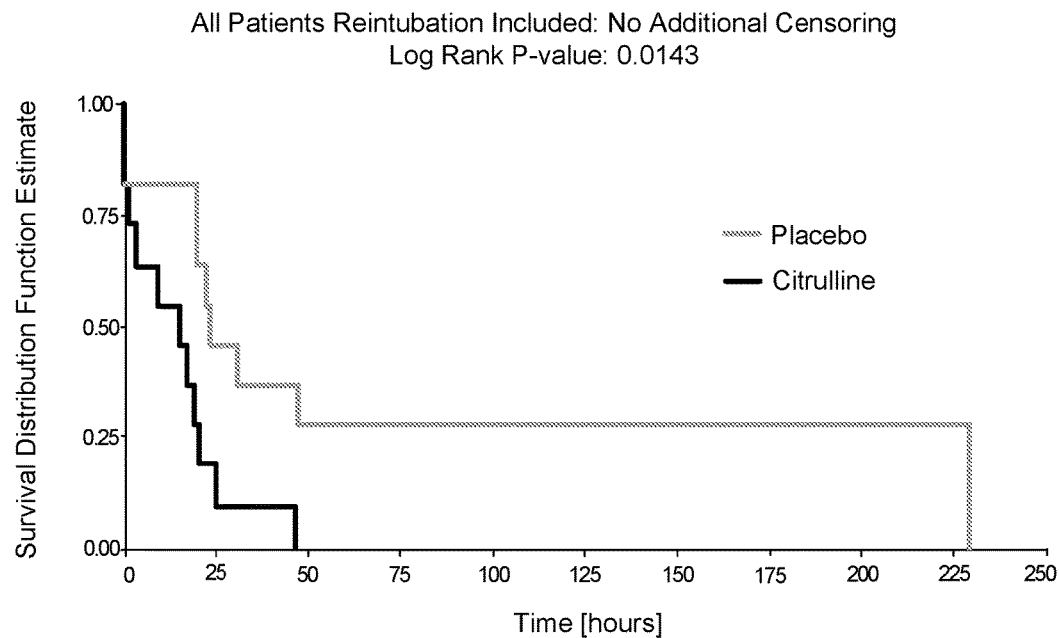
FIG. 33A-B depicts the composite endpoint is the maximum length of the duration of mechanical ventilation and the duration of inotrope use.
Figure 33B:
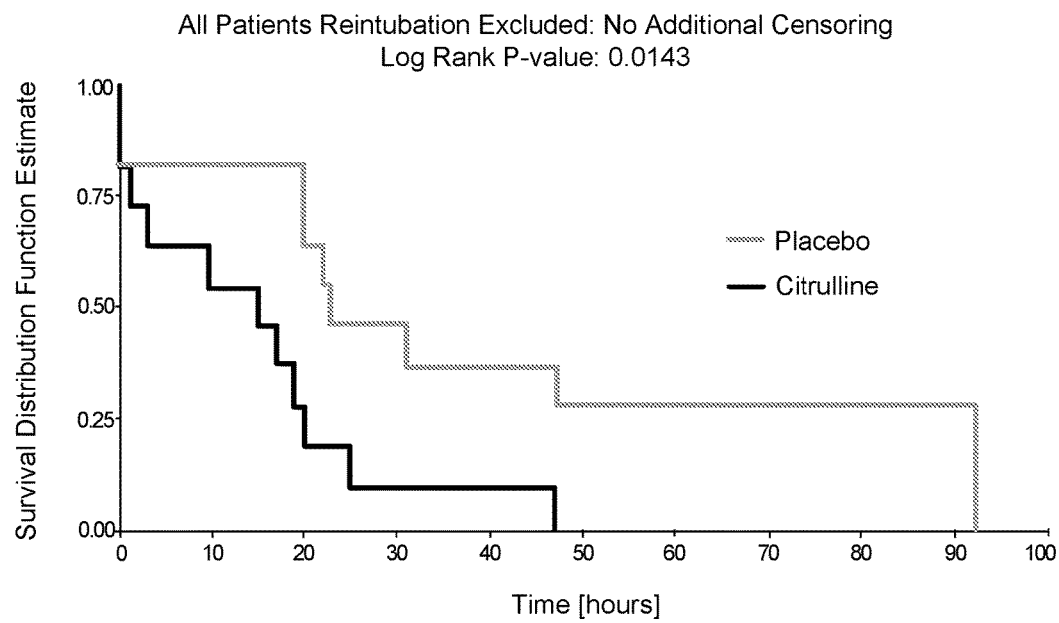

Kaplan-Meier plots of the composite endpoint are presented with re-intubation times included and excluded in FIG. 33. In both analyses, patients with inotrope use still ongoing at 48 hours and mechanical ventilation of less than 48 hours were censored. In both analyses, citrulline-treated patients required statistically significantly less mechanical ventilation or inotropes than placebo-treated patients.

Example 10H

Duration of Hospitalization

Duration of hospitalization was calculated as the total number of days postoperative until discharge from the hospital. The average duration of hospitalization was lower in the citrulline than the placebo treatment group, however, the difference was not statistically significant (Table 17).

TABLE 17

Duration of hospitalization

| | Placebo (N = 11) | Citrulline (N = 11) | Diff (CI) t-test p-value Wilcoxon rank-sum test p-value |
|---|---|---|---|
| Duration of hospitalization [days] | | | |
| Mean ± SD | 8.4 ± 9.38 | 4.6 ± 1.21 | 3.7 (−2.2, 9.7) 0.2062 |
| Median | 5.0 | 5.0 | 0.2637 |
| Range | 4.0-36.0 | 3.0-7.0 | |

Pharmacokinetics and Clinical Outcomes For Examples 10A-10H

The results of the PK and clinical outcome analyses in EXAMPLES 10A-10H showed either statistically significant results or as strong trends supporting that the protocols described herein may be used to maintain plasma citrulline levels and, consequently, reduce the incidence and severity of cardio-pulmonary bypass pulmonary injury. The methods described herein achieved target plasma citrulline levels >100 μmol/L in patients receiving citrulline. The duration of mechanical ventilation was reduced in patients receiving citrulline as compared to patients receiving placebo. The duration of the use of inotropes to support cardiac output was reduced in patients receiving citrulline as compared to patients receiving placebo. The overall duration of treatment with concomitant vasoactive medication was shorter in citrulline—than placebo-treated patients. The overall need for respiratory support was lower in the citrulline compared to the placebo treatment group. Patients receiving study drug exhibited shorter composite durations of positive pressure ventilation and inotrope therapy than did patients receiving placebo. Thus, as assessed by the composite surrogate marker variable, patients receiving citrulline were ready for discharge from the ICU sooner than patients receiving placebo. This was also shown in analyses of the duration of ICU stay and in the analysis of the longest duration of mechanical ventilation, i.v. inotrope use or vasodilator use. Similarly, the overall duration of hospitalization was shorter in citrulline-treated patients compared to placebo-treated patients.

The methods described herein comprising the administration of IV L-citrulline delivery given peri-operatively achieve a plasma citrulline level of >100 μmol/L during follow-up in children undergoing surgical repair of an atrial septal defect (ASD) and/or a ventricular septal defect (VSD) or a partial or complete atrioventricular septal defect (AVSD). In addition, citrulline treatment lead to an unexpected decreased PVT and in consequence the need for prolonged postoperative invasive mechanical ventilation associated with surgical repair of congenital cardiac lesions.

The results show that the administered doses (bolus and infusion) of IV citrulline achieved sustained, high citrulline plasma levels above the target level. Across all sampling time points analyzed, the mean citrulline concentration in the citrulline treatment group exceeded the specified lower limit of 100 μmol/L, whereas the mean citrulline concentrations in the placebo group were below this threshold at all time points analyzed. The difference in the number of samples with citrulline concentrations above the target level was highly statistically significant (p=0.0006) in favor of citrulline treatment.

Patients receiving citrulline in accordance with the methods described herein also showed shorter composite durations of mechanical ventilation and inotrope therapy than did patients receiving placebo. Thus, as assessed by the composite surrogate marker variable, patients receiving study drug were ready for discharge from the ICU sooner than patients receiving placebo.

Levels of nitric oxide (NO) did not change notably during citrulline or placebo treatment. This finding can be explained by the very local production of nitric oxide. Citrulline treatment is expected to improve the local tightly-regulated NO production, but changes in NO may not be recordable in the bloodstream.

Safety data collected in the study showed that L-citrulline administration was safe and no unexpected AEs and/or SAEs occurred under this treatment. All patients (100%) in the citrulline group and 73% of patients in the placebo group experienced at least one treatment-emergent AE. In patients treated with citrulline, the most frequent AEs were pleural effusion (36%), tachypnea (27%), hypertension (27%), and hypotension (27%). The most frequent AEs in the placebo arm were pleural effusion (45%), hypertension (36%), nodal rhythm (27%), and vomiting (27%). No AE leading to death, no SAE, and no AE leading to discontinuation were reported.

There was no difference in post-operative bleeding between the 2 treatment groups, as indicated by the length and volume of chest tube drainage. Study treatment had no apparent impact on most of the laboratory parameters investigated for safety reasons. Up to 24 hours after the start of treatment, AST levels as well as total bilirubin concentration at least doubled in both treatment groups, while mean ALKP levels. BUN remained stable in the placebo group, while it increased from baseline through to Day 2 in the citrulline group (p=0.0111).

Heart rate was consistently higher in the placebo group than the citrulline group. There was no noteworthy impact of treatment on oxygen saturation or systemic arterial blood pressure. Overall, the results of this study indicate that intravenous administration of citrulline in accordance with the methods described herein treatment can play a beneficial role in preventing the clinical sequelae of CPB-induced lung injury by preventing the uncoupling of the eNOS enzyme during surgery.

While the foregoing invention has been described in connection with this preferred embodiment, it is not to be limited thereby but is to be limited solely by the scope of the claims which follow.

What is claimed is:

1. A method for maintaining the coupling of endothelial nitric oxide synthase (eNOS) to reduce the incidence or severity of cardiopulmonary bypass-induced pulmonary injury due to free radical formation in a patient during cardiopulmonary bypass comprising administering an effective amount of citrulline to the patient before, during, and after the surgery, wherein the citrulline administered at the initiation of the surgery is about 100-500 mg/kg of citrulline, wherein the citrulline administered during the surgery is added to hemoconcentration replacement fluid during the surgery, wherein the effective amount of citrulline is an amount sufficient to reduce the uncoupling of endothelial nitric oxide synthase (eNOS).

2. The method of claim 1, wherein the effective amount of citrulline is an amount sufficient to reduce the formation of free radicals.

3. The method of claim 1, wherein the effective amount of citrulline is an amount sufficient to reduce the incidence or severity of cardiopulmonary bypass-induced pulmonary injury.

4. The method of claim 1, wherein the citrulline is administered prior to the surgery is administered at about 12 hours prior to the surgery.

5. The method of claim 1, wherein the surgery is to correct a cardiac defect.

6. The method of claim 1, wherein the citrulline added during the surgery is added at about 100-500 µmol/L.

7. The method of claim 1, wherein citrulline is administered after the surgery is administered to the patient for about 12-48 hours after surgery at about 3-12 mg/kg/hour.

8. The method of claim 1, wherein the citrulline is administered orally, intravenously, by inhalation, or a combination thereof.

9. The method of claim 1, wherein the patient's plasma citrulline level is raised above 100 µmol/L.

10. The method of claim 1, wherein the patient's plasma citrulline level is raised above about 100 µmol/L postoperatively.

11. The method of claim 1, wherein the patient is a neonate, pre-adolescent, adolescent, or an adult.

12. The method of claim 1, wherein the patient is a preterm infant.

13. The method of claim 1, wherein the patient's intensive care unit (ICU) stay is decreased.

14. The method of claim 1, wherein the patient's intensive care unit (ICU) stay is decreased to less than 27 days.

* * * * *

UNITED STATES PATENT AND TRADEMARK OFFICE
CERTIFICATE OF CORRECTION

PATENT NO. : 10,265,286 B2
APPLICATION NO. : 15/853248
DATED : April 23, 2019
INVENTOR(S) : Marshall L. Summar et al.

It is certified that error appears in the above-identified patent and that said Letters Patent is hereby corrected as shown below:

On the Title Page

In item (72) the inventor name reads as follows:
Frederick W. Barr

Should read as follows:
--Frederick E. Barr--

Signed and Sealed this
Fourteenth Day of February, 2023

Katherine Kelly Vidal
*Director of the United States Patent and Trademark Office*